US006635427B2

United States Patent
Wittwer et al.

(10) Patent No.: US 6,635,427 B2
(45) Date of Patent: Oct. 21, 2003

(54) SINGLE-LABELED OLIGONUCLEOTIDE PROBES FOR HOMOGENEOUS NUCLEIC ACID SEQUENCE ANALYSIS

(75) Inventors: Carl T. Wittwer, Salt Lake City, UT (US); Andrew O. Crockett, West Valley, UT (US); Brian E. Caplin, Salt Lake City, UT (US); Wade Stevenson, West Jordan, UT (US); Jian Chen, Sandy, UT (US); Noriko Kusukawa, Salt Lake City, UT (US)

(73) Assignees: University of Utah Research Foundation, Salt Lake City, UT (US); Idaho Technology, Salt Lake City, UT (US)

(*) Notice: Subject to any disclaimer, the term of this patent is extended or adjusted under 35 U.S.C. 154(b) by 30 days.

(21) Appl. No.: 09/927,842

(22) Filed: Aug. 10, 2001

(65) Prior Publication Data

US 2003/0022177 A1 Jan. 30, 2003

Related U.S. Application Data

(60) Provisional application No. 60/224,726, filed on Aug. 11, 2000, and provisional application No. 60/240,610, filed on Oct. 16, 2000.

(51) Int. Cl.$^7$ .......................... C12Q 1/68; C12P 19/34; C07H 21/04

(52) U.S. Cl. .......................... 435/6; 435/91.2; 536/24.3

(58) Field of Search .......................... 435/6, 91.2, 810; 536/24.3

(56) References Cited

U.S. PATENT DOCUMENTS

| | | | | |
|---|---|---|---|---|
| 5,691,146 A | 11/1997 | Mayrand | ....................... | 435/6 |
| 5,716,784 A | 2/1998 | Di Cesare | ...................... | 435/6 |
| 5,888,739 A | 3/1999 | Pitner et al. | .................... | 435/6 |
| 5,994,056 A | 11/1999 | Higuchi | .......................... | 435/6 |
| 6,030,787 A | 2/2000 | Livak et al. | .................... | 435/6 |
| 6,174,670 B1 | 1/2001 | Wittwer et al. | ................. | 435/6 |
| 6,465,175 B2 * | 10/2002 | Horn et al. | ..................... | 435/6 |
| 6,492,121 B2 * | 12/2002 | Kurane et al. | ................. | 435/6 |
| 6,495,326 B2 * | 12/2002 | Kurane et al. | ................. | 435/6 |
| 2001/0000148 A1 | 4/2001 | Kurane et al. | ................. | 435/6 |

FOREIGN PATENT DOCUMENTS

| | | |
|---|---|---|
| DE | 198 58 588 | 2/2000 |
| EP | 0 710 668 A2 | 8/1996 |
| WO | WO 97/43451 A1 | 11/1997 |
| WO | WO 97/46714 A1 | 12/1997 |
| WO | WO 98/26093 | 6/1998 |
| WO | WO 99/13105 | 3/1999 |
| WO | WO 01/02558 A1 | 1/2001 |
| WO | WO 01/73118 A2 | 10/2001 |

OTHER PUBLICATIONS

Talavera et al., "Fluorescein–Labeled DNA Probes for Homogeneous Hybridization Assays: Application to DNA *E. coli* Renaturation", *Applied Spectroscopy*, vol 51, No. 3, pp. 401–406, (1997).

Crockett et al., "Fluorescein–labeled Oligonucleotides for Real–Time PCT: Using the Inherent Quenching of Deoxyguanosisn Nucleotides", *Analytical Biochemistry*, 290, pp. 89–97, (2001).

Cooper et al., "Analysis of Fluorescence Energy Transfer in Duplex and Branched DNA Molecules", *Biochemistry* 29:9261–9268, (1990).

Der–Balian et al., "Fluorescein Labeling of Fab while Preserving Single Thiol", *Analytical Biochemistry*, 173:9, 59–63, (1988).

Ishiguro et al., "Fluorescence detection of specific sequence of nucleic acids by oxazole yellow–linked oligonucleotides. Homogeneous quantitative monitoring of in vitro transcription" *Nucleic Acids Research*, 24:4992–4997, (1996).

Kumke et al., "Temperature and Quenching Studies of Fluorescence Polarization Detection on DNA Hybridization", *Anal. Chem.*, 69:500–506, (1997).

Lay et al., "Real–time fluorescence genotyping of factor V Leiden during rapid–cycle PCR", *Clinical Chemistry*, 43, No. 12: 2262–2267, (1997).

Lee et al., "A Fluorometric Assay for DNA Cleavage Reactions Characterized with BamHI Restriction Endonuclease", *Analytical Biochemistry*, 220:377–383, (1994).

Livak et al., "Oligonucleotides with Fluorescent Dyes at Opposite Ends Provide a Quenched Probe System Useful for Detecting PCR Product and Nucleic Acid Hybridization", *PCR Methods and Applications*, 4:357–362, (1995).

Schütz et al., "Spreadsheet Software for Thermodynamic Melting Point Prediction of Oligonucleotide Hybridization with and without Mismatches", *BioTechniques* 27:1218–1224, (1999).

Seidel et al., "Nucleobase–Specific Quenching of Fluorescent Dyes", *J. Phys Chem*, 100:5541–5553, (1996).

Sjöback et al., "Absorption and fluorescence properties of fluorescein", *Spectrochim Acta*, 51A, L7, (1995).

(List continued on next page.)

*Primary Examiner*—Kenneth R. Horlick
(74) *Attorney, Agent, or Firm*—Barnes & Thornburg

(57) ABSTRACT

Probes and methods are provided for detection and analysis of nucleic acid sequences. The probes are single-labeled oligonucleotide probes whose fluorescence emission changes in response to probe-target hybridization and dissociation. The methods are for analyzing one or multiple nucleic acid loci using the probes. This invention further relates to the use of fluorescence changes in single-labeled probes for melting curve analysis, genotyping, and pathogen detection, and to methods for quantification of specific sequences in real-time monitoring of nucleic acid amplification.

40 Claims, 13 Drawing Sheets

OTHER PUBLICATIONS

Tyagi et al., "Molecular Beacons: Probes that Fluoresce upon Hybridization", *Nature Biotechnology*, 4:359–363, (1998).

Walter et al., "Real–time monitoring of hairpin ribozyme kinetics through base–specific quenching of fluorescein–labeled substrates", *RNA*, 3:392–404., (1997).

Whitcombe et al., "Detection of PCR products using self-probing amplicons and fluorescence", *Nature Biotechnology* 17:804–807, (1999.

Wittwer et al., "Continuous Fluorescence Monitoring of Rapid Cycle DNA Amplification", *BioTechniques*, 22:130–138, (1997).

Yguerabide et al., "Pyrene–Labeled DNA Probes for Homogeneous Detection of Complementary DNA Sequences: Poly(C) Model System", *Analytical Biochemistry*, 241:238–247, (1996).

* cited by examiner

SEQUENCE LISTING

<160> NUMBER OF SEQ ID NOS: 71

<210> SEQ ID NO 1
<211> LENGTH: 19
<212> TYPE: DNA
<213> ORGANISM: Salmonella sp.

<400> SEQUENCE: 1
tggatgattt agtgtttgc                                                    19

<210> SEQ ID NO 2
<211> LENGTH: 20
<212> TYPE: DNA
<213> ORGANISM: Salmonella sp.

<400> SEQUENCE: 2
cgcccgtaag agagtaaaac                                                   20

<210> SEQ ID NO 3
<211> LENGTH: 21
<212> TYPE: DNA
<213> ORGANISM: Salmonella sp.

<400> SEQUENCE: 3
ccaaaaggca gcgtctgttc c                                                 21

<210> SEQ ID NO 4
<211> LENGTH: 20
<212> TYPE: DNA
<213> ORGANISM: Salmonella sp.

<400> SEQUENCE: 4
ccaaaaggca gcgtctgttc                                                   20

<210> SEQ ID NO 5
<211> LENGTH: 20

-continued

```
<212> TYPE: DNA
<213> ORGANISM: Salmonella sp.

<400> SEQUENCE: 5
caaaaggcag cgtctgttcc                                            20

<210> SEQ ID NO 6
<211> LENGTH: 19
<212> TYPE: DNA
<213> ORGANISM: Salmonella sp.

<400> SEQUENCE: 6
ccaaaaggca gcgtctgtt                                             19

<210> SEQ ID NO 7
<211> LENGTH: 18
<212> TYPE: DNA
<213> ORGANISM: Salmonella sp.

<400> SEQUENCE: 7
caaaaggcag cgtctgtt                                              18

<210> SEQ ID NO 8
<211> LENGTH: 18
<212> TYPE: DNA
<213> ORGANISM: Salmonella sp.

<400> SEQUENCE: 8
aaaaggcagc gtctgttc                                              18

<210> SEQ ID NO 9
<211> LENGTH: 19
<212> TYPE: DNA
<213> ORGANISM: Salmonella sp.

<400> SEQUENCE: 9
aaaaggcagc gtctgttcc                                             19

<210> SEQ ID NO 10
<211> LENGTH: 17
<212> TYPE: DNA
<213> ORGANISM: Salmonella sp.

<400> SEQUENCE: 10
aaaaggcagc gtctgtt                                               17

<210> SEQ ID NO 11
<211> LENGTH: 23
<212> TYPE: DNA
<213> ORGANISM: Salmonella sp.

<400> SEQUENCE: 11
aggaacagac gctgccttt tggc                                        23

<210> SEQ ID NO 12
<211> LENGTH: 23
<212> TYPE: DNA
<213> ORGANISM: Salmonella sp.

<400> SEQUENCE: 12
aggaacagac gctacctttt ggc                                        23

<210> SEQ ID NO 13
```

```
<211> LENGTH: 23
<212> TYPE: DNA
<213> ORGANISM: Salmonella sp.

<400> SEQUENCE: 13
aggaacaaac gctaccttttt ggc                                         23

<210> SEQ ID NO 14
<211> LENGTH: 18
<212> TYPE: DNA
<213> ORGANISM: Homo sapiens

<400> SEQUENCE: 14
ctgtattcct cgcctgtc                                                18

<210> SEQ ID NO 15
<211> LENGTH: 17
<212> TYPE: DNA
<213> ORGANISM: Homo sapiens

<400> SEQUENCE: 15
tgtattcctc gcctgtc                                                 17

<210> SEQ ID NO 16
<211> LENGTH: 17
<212> TYPE: DNA
<213> ORGANISM: Homo sapiens

<400> SEQUENCE: 16
ctgtattcct cgcctgt                                                 17

<210> SEQ ID NO 17
<211> LENGTH: 22
<212> TYPE: DNA
<213> ORGANISM: Homo sapiens

<400> SEQUENCE: 17
tggacaggcg aggaatacag gt                                           22

<210> SEQ ID NO 18
<211> LENGTH: 22
<212> TYPE: DNA
<213> ORGANISM: Homo sapiens

<400> SEQUENCE: 18
tggacaggca aggaatacag gt                                           22

<210> SEQ ID NO 19
<211> LENGTH: 22
<212> TYPE: DNA
<213> ORGANISM: Homo sapiens

<400> SEQUENCE: 19
gagagacatc gcctctgggc ta                                           22

<210> SEQ ID NO 20
<211> LENGTH: 20
<212> TYPE: DNA
<213> ORGANISM: Homo sapiens

<400> SEQUENCE: 20
tgttatcaca ctggtgctaa                                              20
```

```
<210> SEQ ID NO 21
<211> LENGTH: 22
<212> TYPE: DNA
<213> ORGANISM: Homo sapiens

<400> SEQUENCE: 21
ctgactcctg tggagaagtc tg                                              22

<210> SEQ ID NO 22
<211> LENGTH: 21
<212> TYPE: DNA
<213> ORGANISM: Homo sapiens

<400> SEQUENCE: 22
tgactcctgt ggagaagtct g                                               21

<210> SEQ ID NO 23
<211> LENGTH: 27
<212> TYPE: DNA
<213> ORGANISM: Homo sapiens

<400> SEQUENCE: 23
cggcagactt ctcctcagga gtcaggt                                         27

<210> SEQ ID NO 24
<211> LENGTH: 27
<212> TYPE: DNA
<213> ORGANISM: Homo sapiens

<400> SEQUENCE: 24
cggcagactt ctccacagga gtcaggt                                         27

<210> SEQ ID NO 25
<211> LENGTH: 27
<212> TYPE: DNA
<213> ORGANISM: Homo sapiens

<400> SEQUENCE: 25
cggcagactt ctccttagga gtcaggt                                         27

<210> SEQ ID NO 26
<211> LENGTH: 20
<212> TYPE: DNA
<213> ORGANISM: Homo sapiens

<400> SEQUENCE: 26
acacaactgt gttcactagc                                                 20

<210> SEQ ID NO 27
<211> LENGTH: 20
<212> TYPE: DNA
<213> ORGANISM: Homo sapiens

<400> SEQUENCE: 27
caacttcatc cacgttcacc                                                 20

<210> SEQ ID NO 28
<211> LENGTH: 23
<212> TYPE: DNA
<213> ORGANISM: Homo sapiens

<400> SEQUENCE: 28
tgcgtgatga tgaaatcggc tcc                                             23
```

<210> SEQ ID NO 29
<211> LENGTH: 22
<212> TYPE: DNA
<213> ORGANISM: Homo sapiens

<400> SEQUENCE: 29
tgcgtgatga tgaaatcggc tc                                             22

<210> SEQ ID NO 30
<211> LENGTH: 21
<212> TYPE: DNA
<213> ORGANISM: Homo sapiens

<400> SEQUENCE: 30
tgcgtgatga tgaaatcggc t                                              21

<210> SEQ ID NO 31
<211> LENGTH: 27
<212> TYPE: DNA
<213> ORGANISM: Homo sapiens

<400> SEQUENCE: 31
cgggagccga tttcatcatc acgcagc                                        27

<210> SEQ ID NO 32
<211> LENGTH: 27
<212> TYPE: DNA
<213> ORGANISM: Homo sapiens

<400> SEQUENCE: 32
cgggagtcga tttcatcatc acgcagc                                        27

<210> SEQ ID NO 33
<211> LENGTH: 23
<212> TYPE: DNA
<213> ORGANISM: Homo sapiens

<400> SEQUENCE: 33
tgaaggagaa ggtgtctgcg gga                                            23

<210> SEQ ID NO 34
<211> LENGTH: 20
<212> TYPE: DNA
<213> ORGANISM: Homo sapiens

<400> SEQUENCE: 34
aggacggtgc ggtgagagtg                                                20

<210> SEQ ID NO 35
<211> LENGTH: 20
<212> TYPE: DNA
<213> ORGANISM: Homo sapiens

<400> SEQUENCE: 35
tctcagcaag cctcaatgct                                                20

<210> SEQ ID NO 36
<211> LENGTH: 25
<212> TYPE: DNA
<213> ORGANISM: Homo sapiens

<400> SEQUENCE: 36
gggagcattg aggctcgctg agagt                                          25

```
<210> SEQ ID NO 37
<211> LENGTH: 25
<212> TYPE: DNA
<213> ORGANISM: Homo sapiens

<400> SEQUENCE: 37
gggagcattg aggcttgctg agagt                                              25

<210> SEQ ID NO 38
<211> LENGTH: 24
<212> TYPE: DNA
<213> ORGANISM: Homo sapiens

<400> SEQUENCE: 38
attgatcagt ttggagagta gggg                                               24

<210> SEQ ID NO 39
<211> LENGTH: 21
<212> TYPE: DNA
<213> ORGANISM: Homo sapiens

<400> SEQUENCE: 39
gagctgccca tgaatagcac t                                                  21

<210> SEQ ID NO 40
<211> LENGTH: 28
<212> TYPE: DNA
<213> ORGANISM: Homo sapiens

<400> SEQUENCE: 40
cacacggcga ctctcatcat catagaac                                           28

<210> SEQ ID NO 41
<211> LENGTH: 27
<212> TYPE: DNA
<213> ORGANISM: Homo sapiens

<400> SEQUENCE: 41
acacggcgac tctcatcatc atagaac                                            27

<210> SEQ ID NO 42
<211> LENGTH: 27
<212> TYPE: DNA
<213> ORGANISM: Homo sapiens

<400> SEQUENCE: 42
cacacggcga ctctcatcat catagaa                                            27

<210> SEQ ID NO 43
<211> LENGTH: 31
<212> TYPE: DNA
<213> ORGANISM: Homo sapiens

<400> SEQUENCE: 43
tgttctatga tcatgagagt cgccgtgtgg a                                       31

<210> SEQ ID NO 44
<211> LENGTH: 31
<212> TYPE: DNA
<213> ORGANISM: Homo sapiens

<400> SEQUENCE: 44
```

-continued tgttctatga tgatgagagt cgccgtgtgg a          31

<210> SEQ ID NO 45
<211> LENGTH: 20
<212> TYPE: DNA
<213> ORGANISM: Homo sapiens

<400> SEQUENCE: 45
cacatggtta aggcctgttg                       20

<210> SEQ ID NO 46
<211> LENGTH: 20
<212> TYPE: DNA
<213> ORGANISM: Homo sapiens

<400> SEQUENCE: 46
gatcccaccc tttcagactc                       20

<210> SEQ ID NO 47
<211> LENGTH: 21
<212> TYPE: DNA
<213> ORGANISM: Homo sapiens

<400> SEQUENCE: 47
cacctggcac gtatatctct g                     21

<210> SEQ ID NO 48
<211> LENGTH: 20
<212> TYPE: DNA
<213> ORGANISM: Homo sapiens

<400> SEQUENCE: 48
acctggcacg tatatctctg                       20

<210> SEQ ID NO 49
<211> LENGTH: 25
<212> TYPE: DNA
<213> ORGANISM: Homo sapiens

<400> SEQUENCE: 49
agcagagata tacgtgccag gtgga                 25

<210> SEQ ID NO 50
<211> LENGTH: 25
<212> TYPE: DNA
<213> ORGANISM: Homo sapiens

<400> SEQUENCE: 50
agcagagata tacgtaccag gtgga                 25

<210> SEQ ID NO 51
<211> LENGTH: 20
<212> TYPE: DNA
<213> ORGANISM: Homo sapiens

<400> SEQUENCE: 51
tggcaagggt aaacagatcc                       20

<210> SEQ ID NO 52
<211> LENGTH: 20
<212> TYPE: DNA
<213> ORGANISM: Homo sapiens

<400> SEQUENCE: 52
tacctcctca ggcactcctc                                                    20

<210> SEQ ID NO 53
<211> LENGTH: 27
<212> TYPE: DNA
<213> ORGANISM: Homo sapiens

<400> SEQUENCE: 53
ataggaaaca ccaaagatga tattttc                                            27

<210> SEQ ID NO 54
<211> LENGTH: 26
<212> TYPE: DNA
<213> ORGANISM: Homo sapiens

<400> SEQUENCE: 54
ataggaaaca ccaaagatga tatttt                                             26

<210> SEQ ID NO 55
<211> LENGTH: 30
<212> TYPE: DNA
<213> ORGANISM: Homo sapiens

<400> SEQUENCE: 55
agaaaatatc atctttggtg tttcctatga                                         30

<210> SEQ ID NO 56
<211> LENGTH: 27
<212> TYPE: DNA
<213> ORGANISM: Homo sapiens

<400> SEQUENCE: 56
agaaaatatc attggtgttt cctatga                                            27

<210> SEQ ID NO 57
<211> LENGTH: 20
<212> TYPE: DNA
<213> ORGANISM: Homo sapiens

<400> SEQUENCE: 57
ggaggcaagt gaatcctgag                                                    20

<210> SEQ ID NO 58
<211> LENGTH: 20
<212> TYPE: DNA
<213> ORGANISM: Homo sapiens

<400> SEQUENCE: 58
cctcttctag ttggcatgct                                                    20

<210> SEQ ID NO 59
<211> LENGTH: 21
<212> TYPE: DNA
<213> ORGANISM: Salmonella sp.
<220> FEATURE:
<221> NAME/KEY: misc_feature
<222> LOCATION: (9)..(9)
<223> OTHER INFORMATION: fluorescent label inserted as virtual
      nucleotide

<400> SEQUENCE: 59
ccaaaaggna gcgtctgttc c                                                  21

```
<210> SEQ ID NO 60
<211> LENGTH: 10
<212> TYPE: DNA
<213> ORGANISM: Homo sapiens

<400> SEQUENCE: 60
gcctgccctt                                                              10

<210> SEQ ID NO 61
<211> LENGTH: 10
<212> TYPE: DNA
<213> ORGANISM: Homo sapiens

<400> SEQUENCE: 61
cgacacgcta                                                              10

<210> SEQ ID NO 62
<211> LENGTH: 27
<212> TYPE: DNA
<213> ORGANISM: Homo sapiens

<400> SEQUENCE: 62
ccaggaaaac atagtaaaaa atggaat                                           27

<210> SEQ ID NO 63
<211> LENGTH: 30
<212> TYPE: DNA
<213> ORGANISM: Homo sapiens

<400> SEQUENCE: 63
gaatcgtggt ttatcaagtc attaaaatca                                        30

<210> SEQ ID NO 64
<211> LENGTH: 31
<212> TYPE: DNA
<213> ORGANISM: Homo sapiens

<400> SEQUENCE: 64
gtgttgatac ttgaacatta tttagctaca a                                      31

<210> SEQ ID NO 65
<211> LENGTH: 36
<212> TYPE: DNA
<213> ORGANISM: Homo sapiens
<220> FEATURE:
<221> NAME/KEY: modified_base
<222> LOCATION: (36)..(36)
<223> OTHER INFORMATION: fluorescein-labelled cytosine

<400> SEQUENCE: 65
cttgatgagg atcccaaaga ccacccccaa gaccan                                 36

<210> SEQ ID NO 66
<211> LENGTH: 19
<212> TYPE: DNA
<213> ORGANISM: Homo sapiens
<220> FEATURE:
<221> NAME/KEY: modified_base
<222> LOCATION: (1)..(1)
<223> OTHER INFORMATION: Blackhole Quencher dye-labelled adenosine

<400> SEQUENCE: 66
nccagcagaa tgccaacca                                                    19

<210> SEQ ID NO 67
```

```
<211> LENGTH: 22
<212> TYPE: DNA
<213> ORGANISM: Homo sapeins
<220> FEATURE:
<221> NAME/KEY: misc_feature
<222> LOCATION: (11)..(11)
<223> OTHER INFORMATION: fluorescein inserted as virtual nucleotide

<400> SEQUENCE: 67
ctgtattcct ngcctgtcca gg                                          22

<210> SEQ ID NO 68
<211> LENGTH: 28
<212> TYPE: DNA
<213> ORGANISM: Homo sapiens

<400> SEQUENCE: 68
agaataaatg ttatcacact ggtgctaa                                    28

<210> SEQ ID NO 69
<211> LENGTH: 18
<212> TYPE: DNA
<213> ORGANISM: Homo sapiens

<400> SEQUENCE: 69
gacatcgcct ctgggcta                                               18

<210> SEQ ID NO 70
<211> LENGTH: 15
<212> TYPE: DNA
<213> ORGANISM: Homo sapiens
<220> FEATURE:
<221> NAME/KEY: misc_feature
<222> LOCATION: (15)..(15)
<223> OTHER INFORMATION: fluorescein-labelled guanine

<400> SEQUENCE: 70
ggcgaggaat acagg                                                  15

<210> SEQ ID NO 71
<211> LENGTH: 21
<212> TYPE: DNA
<213> ORGANISM: Homo sapiens

<400> SEQUENCE: 71
ggctggataa ccttggctgt a                                           21
```

SINGLE-LABELED OLIGONUCLEOTIDE PROBES FOR HOMOGENEOUS NUCLEIC ACID SEQUENCE ANALYSIS

This application claims priority under 35 U.S.C. §119(e) to U.S. Provisional Application No. 60/224,726, filed Aug. 11, 2000, and U.S. Provisional Application No. 60/240,610, filed Oct. 16, 2000, which are expressly incorporated by reference herein.

FIELD OF INVENTION

The invention relates to a method for homogeneous detection and analysis of nucleic acid sequences by use of single-labeled oligonucleotide probes whose fluorescence emission changes in response to probe-target hybridization and dissociation, and more particularly, to methods for analyzing one or multiple nucleic acid loci using said probes. This invention further relates to the use of fluorescence changes in single-labeled probes for melting curve analysis, genotyping, and pathogen detection, and to a method for quantification of specific sequences in real-time monitoring of nucleic acid amplification.

BACKGROUND AND SUMMARY OF THE INVENTION

Probe hybridization is a widely used method for the detection, analysis, and quantification of nucleic acid sequences. Common techniques include Southern hybridization, dot blotting, gel-shift assays, and solution-based homogeneous assays, and are often coupled with polymerase chain reaction (PCR). The basic devices used in these techniques include electrophoresis gels, DNA arrays immobilized on surfaces of glass slides, beads, membranes or microtiter plates, and instrumentation for homogeneous assays such as the LightCycler system (Roche Molecular Biochemicals), the ABI PRISM7700 sequence detection system (PE Applied Biosystems), and the iCycler system (Bio-Rad Laboratories). Homogeneous assays, detection methods that are coupled with amplification processes, perform amplification and analysis in one continuous flow, eliminating or minimizing the need to transfer samples between the two processes. One key element that makes homogenous assays work is a reporter signal generated from probe-target hybridization that is detectable without the need to wash away free probe.

Current homogeneous assays either use nucleic acid-binding dyes such as ethidium bromide and SYBR Green I stain as reporter molecules (Higuchi, U.S. Pat. No. 5,994, 056 and Wittwer et al., U.S. Pat. No. 6,174,670), or they use a minimum of two fluorophores immobilized on probes. The two fluorophores can either be donor-acceptor pairs individually attached to separate oligonucleotides (U.S. Pat. No. 6,174,670, and Di Cesare, U.S. Pat. No. 5,716,784), or they can be reporter-quencher pairs attached to a single oligonucleotide (Mayrand, U.S. Pat. No. 5,691,146, Pitner et al, U.S. Pat. No. 5,888,739 and Livak et al, U.S. Pat. No. 6,030787). Homogeneous assays using DNA binding dyes are convenient, but they provide limited sequence information. Methods based on two-dye systems can provide greater detection specificity, regardless of whether they are donor-acceptor or donor-quencher dye combinations, and are used in systems such as the Hybridization Probe assay (U.S. Pat. No. 6,174,670), the Taqman assay (U.S. Pat. No. 5,691,146), the Molecular Beacon assay (Tyagi et al, 1998. *Nature Biotechnology* 4:359–363) and its variant, the Scorpions primer system (Whitcombe et al, 1999. *Nature Biotechnology* 17:804–807).

In hybridization probe assays, two oligonucleotide probes are used to detect the presence of a particular sequence. Reporter signal is detected when fluorescence resonance energy transfer occurs between the donor dye on one probe and the acceptor on the other by bringing the two dyes into proximity through annealing of probes to target. Once the probes are hybridized, the area under one probe can be studied for possible sequence variances. This can be done by heating the sample and monitoring the temperature at which a loss in signal occurs by dissociation (or "melting") of that probe. Sequence variances may be detected by a shift in the melting temperature (Tm) relative to a reference sample, and such Tm shifts can be predicted using software calculations (Schütz et al, 1999. *BioTechniques* 27:1218–1224). However, the area under the second probe may become a "blind zone" that is not analyzed for sequence variances. The presence of blind zones may be problematic when large segments of DNA need to be analyzed for sequence variances, and multiple probe pairs need to be employed.

The Taqman and molecular beacon assays both use a single oligonucleotide probe with both a reporter and a quencher dye attached. The oligonucleotide probe hybridizes to the target sequence, and the reporter and quencher are separated either by the exonuclease activity of the polymerase or due to change in conformation upon hybridization to the target sequence. Present methods result in relative difficulty in synthesizing these dual-labeled probes. Also, Taqman probes provide an indirect measure of hybridization, as signal continues to be generated once the reporter and quencher are separated by the exonuclease activity of the polymerase.

Changes in fluorescence efficiency of fluorophores by means other than energy transfer have been reported. Various dyes of the fluorescein family are sensitive to pH, and their emission intensities decrease at pHs lower than their pKa, and increase when the pH is close to or higher than the pKa (Sjöback et al, 1995. *Spectrochim Acta* A 51, L7). Also, fluorescein is quenched by more than 50% upon conjugation to biopolymers (Der-Balian et al, 1988. *Analytical Biochemistry* 173:9). These are general fluorescence changes that are induced by external factors. Also known is that the annealing of a fluorescent-labeled oligonucleotide and its unlabeled complementary strand may result in quenching of the probe fluorescence and a shift in the wavelength of emission upon the formation of duplex DNA (Cooper et al 1990. *Biochemistry* 29:9261–9268; Lee et al, 1994. *Analytical Biochemistry* 220:377–383; and Yguerabide et al, 1996. *Analytical Biochemistry* 241:238–247). Fluorescent intensity changes have also been shown using unbound dye and individual nucleotide or nucleoside molecules (Seidel et al, 1996 *J. Phys Chem* 100:5541–5553), RNA substrate-ribozyme interactions (Walter et al, 1997. *RNA* 3:392–404), and nucleic acid duplex formation using probes labeled with asymmetric cyanine dyes (Ishiguro et al 1996. *Nucleic Acids Research* 24:4992–4997; and Svanvik et al 2000. *Analytical Biochemistry* 281:26–35). However, these references do not teach the construction of probes that take advantage of sequence-dependent fluorescence.

Thus, the present invention is directed to oligonucleotide probes wherein each probe has a single fluorescent dye. The oligonucleotide probes are constructed such that hybridization of the probe to a target sequence affects the fluorescent emission of the fluorescent dye. In one embodiment of the invention, hybridization of the probe to the target sequence places the fluorescent dye in close proximity to a guanine residue, with resultant quenching of fluorescent emission. In another embodiment, the fluorescent entity replaces a base in the oligonucleotide probe structure, and upon hybridization this "virtual nucleotide" is placed in a complementary position to a G residue, with resultant quenching of fluorescence. In other embodiments, probes are constructed such that hybridization results in an increase in fluorescent emission. In one such embodiment, the fluorescent entity is attached to a G residue, with increased fluorescence upon hybridization. In another such embodiment, the fluorescent entity is attached to a base analog, with resultant increase in fluorescence upon hybridization. In yet another embodiment of this invention, the fluorescent entity is attached to an internal residue via a flexible linker, with resultant change in fluorescent emission upon hybridization. Finally, various examples of probe systems are provided.

In one aspect of the invention a probe is provided for analyzing a target nucleic acid, the probe comprising a fluorescent detecting entity consisting essentially of an oligonucleotide having a sequence generally complementary to a locus of the target nucleic acid and a fluorescent label linked to a terminal nucleotide of the oligonucleotide, the oligonucleotide sequence of the probe being selected so that upon hybridization of the probe to the locus of the target nucleic acid the fluorescent label is positioned in proximity to a guanine residue of the target nucleic acid with resultant quenching of the fluorescent intensity of the fluorescent label. In one embodiment, the guanine residue is located at position 0, +1, +2, +3, or +4 relative to the position of the flourescent labeled terminal nucleotide.

In another aspect of this invention, a probe is provided for analyzing a target nucleic acid, the probe comprising an oligonucleotide having a sequence generally complementary to a locus of the target nucleic acid and further comprising a residue having a virtual nucleotide wherein a fluorescent dye is substituted for a base, and wherein the magnitude of flourescent emission from the fluorescent dye is altered by hybridization of the probe to the target nucleic acid.

In still another aspect of this invention, a fluorescence-based probe system is provided for analyzing a target nucleic acid, the probe system consisting essentially of a single-labeled polynucleotide comprising a sequence generally complementary to a locus of the nucleic acid and a fluorescent label attached thereto, whereby upon hybridization of the single-labeled polynucleotide to the locus of the nucleic acid the fluorescent label is positioned near a residue of the target nucleic acid with a resultant increase in fluorescent intensity of the fluorescent label. Various embodiments of these augmentation probes are provided.

In yet another aspect of this invention a probe for analyzing a target nucleic acid is provided, the probe comprising a fluorescent detecting entity consisting essentially of a single-labeled oligonucleotide having a sequence generally complementary to a locus of the target nucleic acid and a fluorescent label linked to an internal residue of the oligonucleotide, and wherein oligonucleotide sequence of the probe being selected so that upon hybridization of the probe to the locus of the target nucleic acid the magnitude of fluorescent emission from the fluorescent label is altered by hybridization of the probe to the target nucleic acid.

Additionally, an oligonucleotide probe is provided for detecting the presence of a target nucleic acid from the genus Salmonella the probe comprising a nucleotide sequence selected from the group consisting of

5'CCAAAAGGCAGCGTCTGTTCC (SEQ ID NO:3),

5'CCAAAAGGCAGCGTCTGTTC (SEQ ID NO:4),

5'CAAAAGGCAGCGTCTGTTCC (SEQ ID NO:5),

5'CCAAAAGGCAGCGTCTGTT (SEQ ID NO:6),

5'CAAAAGGCAGCGTCTGTT (SEQ ID NO:7),

5'AAAAGGCAGCGTCTGTTC (SEQ ID NO:8),

5'AAAAGGCAGCGTCTGTTCC (SEQ ID NO:9), and

5'AAAAGGCAGCGTCTGTT (SEQ ID NO:10).

In another aspect of this invention methods are provided using the probes of this invention, in one such embodiment, a method is provided for determining the presence of a target nucleic acid sequence in a biological sample comprising combining a first single-labeled oligonucleotide probe with the sample, said first probe having an oligonucleotide sequence generally complementary to a locus of the target nucleic acid sequence and a fluorescent label linked to an end of the oligonucleotide sequence, the fluorescent label exhibiting an hybridization-dependent fluorescent emission, wherein hybridization of the first probe to the target nucleic acid sequence allows interaction of the fluorescent label with a guanine residue located on the target nucleic acid, thereby decreasing the magnitude of fluorescent emission from the label, illuminating the biological sample, and monitoring the hybridization-dependent fluorescent emission.

In a further aspect of this invention a method is provided for determining the presence of a target nucleic acid sequence in a biological sample comprising combining a single-labeled oligonucleotide probe with the sample, said probe having an oligonucleotide sequence generally complementary to a locus of the target nucleic acid sequence and a fluorescent label linked to a G residue of the oligonucleotide sequence, the fluorescent label exhibiting an hybridization-dependent fluorescent emission, wherein hybridization of the oligonucleotide probe to the target nucleic acid sequence alters interaction of the fluorescent label with the G residue, thereby increasing the fluorescent emission from the label, illuminating the biological sample, and monitoring the hybridization-dependent fluorescent emission.

In still a further aspect of this invention a method is provided for analyzing a sample comprising a target nucleic acid sequence, comprising the steps of combining the sample and an oligonucleotide probe to create a target-probe mixture, wherein the probe includes a virtual nucleotide having a fluorescent label positioned so that the magnitude of fluorescent emission from the fluorescent label is altered by hybridization of the probe to the target nucleic acid sequence, illuminating the mixture, and monitoring the fluorescent emission as a function of temperature.

In an additional aspect of this invention a method is provided for determining the presence a target nucleic acid sequence in a biological sample comprising combining the biological sample with a fluorescent detecting entity consisting essentially of a single-labeled oligonucleotide probe, wherein the single-labeled probe comprises an oligonucleotide having a sequence complementary to a locus of the target nucleic acid sequence, and having a fluorescent label exhibiting an hybridization-dependent emission attached thereto, wherein hybridization of the probe to a selected segment of the target nucleic acid sequence results in an increase in fluorescent emission of the fluorescent label, illuminating the biological sample, and monitoring the hybridization-dependent fluorescent emission. In one such embodiment the fluorescent label is linked to a base of the oligonucleotide probe and the base is selected from the group consisting of 5-nitroindole, 4-nitroindole, 6-nitroindole, and 3-nitropyrrole deoxynucleosides. In another such embodiment, the fluorescent label is attached to a guanine residue and the monitoring step includes monitoring the increased fluorescent emission from the fluorescent label upon hybridization of the probe to the target nucleic acid. In yet another embodiment, the fluorescent label is selected from the group consisting of cyanine dyes and LCRed 705.

An additional aspect of this invention is a kit for analyzing a biological sample comprising a nucleic acid sequence, comprising a fluorescent detecting entity consisting essentially of a single-labeled oligonucleotide probe having an oligonucleotide linked to a fluorescent label, wherein said probe is configured to hybridize to a locus of the segment so that the magnitude of fluorescent emission from the fluorescent label is increased by hybridization of the probe to the locus; and components for amplification of the nucleic acid sequence.

Additional features of the present invention will become apparent to those skilled in the art upon consideration of the following detailed description of preferred embodiments exemplifying the best mode of carrying out the invention as presently perceived.

BRIEF DESCRIPTION OF DRAWINGS

FIG. 4A shows fluorescence vs temperature and FIG. 4B shows the first derivative dF/dT.

FIG. 5A shows no mismatch vs mismatch under fluorescein probe.

FIG. 6 shows homogeneous, real-time factor V Leiden (G1691A) genotyping with an internally labeled fluorescein probe, with melting curve data presented as a first derivative plot. Curves for homozygous wild type (———), homozygous mutant (-------), heterozygous genotypes (··········) are shown.

DETAILED DESCRIPTION OF THE INVENTION

Figure 1:
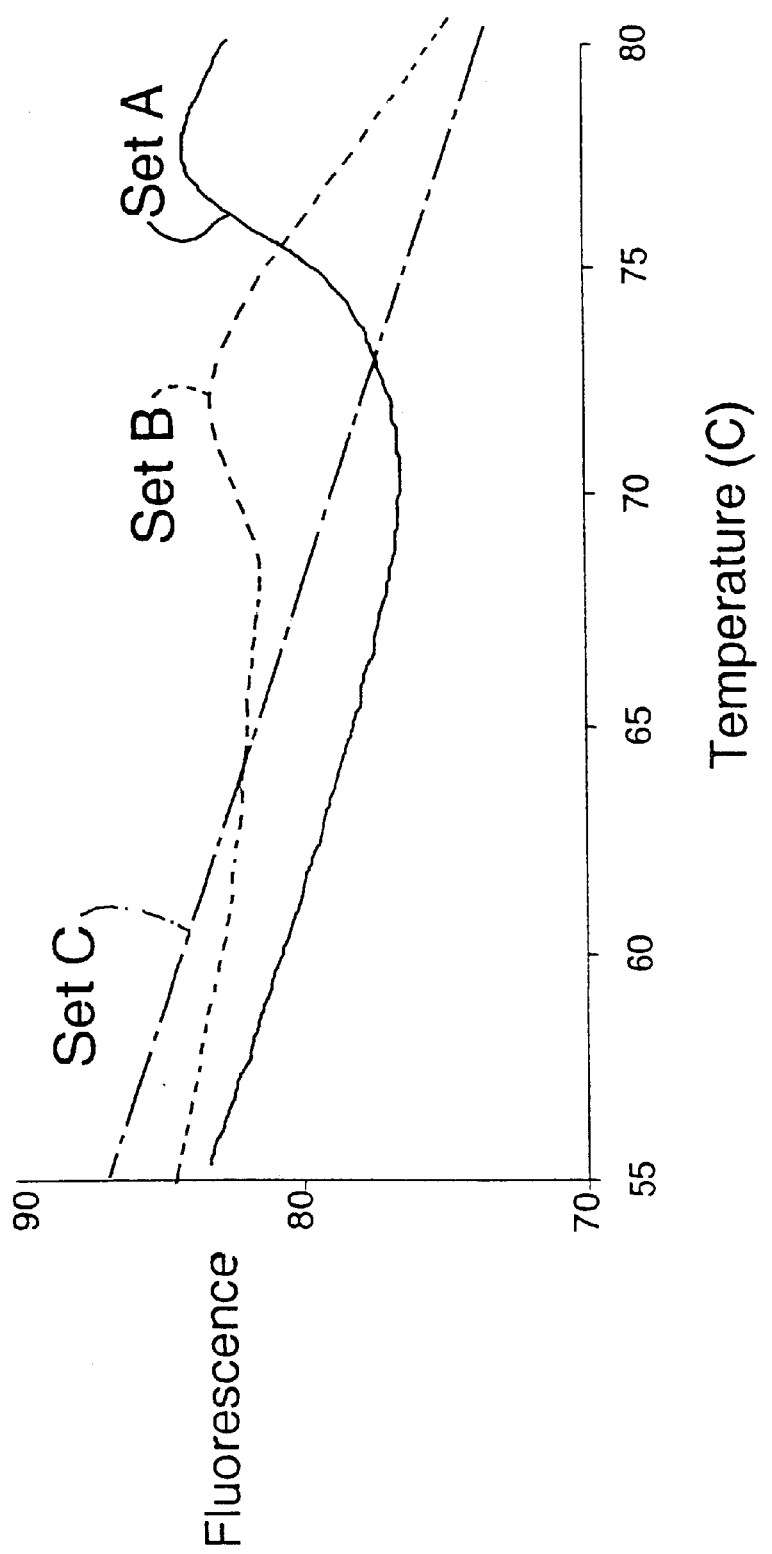
FIG. 1. shows fluorescence acquisition data for the three sets of probes and targets shown in Table 1, Set A (———), Set B (-------), Set C (– – – –).

In an illustrated embodiment, a probe of the invention is used in a homogeneous assay system wherein the detection and analysis of nucleic acid sequences are performed along with the amplification of a target polynucleotide. Alternatively, the probes of the invention may be used in end-point detection assays independent of target amplification. The binding site of the single-labeled oligonucleotide probes is generally located internally on a target nucleic acid, usually between the primers that are used to amplify the target. However, in some embodiments, hybridization of the probe to the target sequence is near or at the end of the target sequence, and in some embodiments the probe-target hybridization forms a blunt end, such as in methods wherein the probe also functions as a primer for target amplification.

The term "oligonucleotide" as used herein includes linear oligomers of natural or modified monomers or linkages including deoxyribonucleosides, ribonucleosides, protein nucleic acid nucleosides, and the like that are capable of specifically binding to a target polynucleotide by base-pairing interactions.

The term "single-labeled oligonucleotide" as used herein includes oligonucleotides having a singular fluorescent label. The label may be provided on the oligonucleotide in various ways, including linked to an end of the phosphate-sugar backbone or to a base of the oligonucleotide, or the dye may be used to replace a base as part of a "virtual nucleotide" structure. However, the term "single-labeled oligonucleotide" excludes constructs having multiple fluorescent dyes attached thereto, such as Taqman probes.

Whenever an oligonucleotide is represented by a sequence of letters, it will be understood that the "A" denotes deoxyadenosine, "T" denotes thymidine, "G" denotes deoxyguanosine, "C" denotes deoxycytidine, unless otherwise noted. "(F)" denotes a fluorescent label.

The term "base," when used to indicate the position in an oligonucleotide, includes base analogs such a 5-nitroindole-2 deoxynucleoside.

The term "complementary" refers to nucleic acid sequences that form a base-paired double helix with each other. When discussing oligonucleotides, "complementary" refers to the opposing strand and when discussing individual bases of an oligonucleotide, "complementary" refers to the position or base on the opposing strand. "Generally complementary" sequences are two nucleic acid sequences that have at least 80% homology. Thus, such sequences may have mismatches but have sufficient homology to form base-paired double helix structures with each other.

According to a method of the invention, a single-labeled probe undergoes changes in fluorescence emission efficiency (or intensity) during the formation and dissociation of a probe-target duplex, the method comprising positioning the probe so that certain conditions are satisfied regarding the location of specific residues on the target strand.

In one embodiment of this invention, the specific residue is a single G residue on the target strand. In this embodiment, fluorescence change upon duplex formation and dissociation is most pronounced when the G is located as the first overhanging nucleotide relative to the fluorescent label (F) as shown diagrammatically below (vertical lines denote base pairing):

```
Probe
   5' (F)XXXXXXXXXXXX   or  5' XXXXXXXXXXXX(F)
       ||||||||||||         ||||||||||||
Target
3'XXXXXXGXXXXXXXXXXXXXX   3' XXXXXXXXXXXXXXXGXXXXX
```

Each of these two positions comprise "Position +1". Fluorescence change, albeit smaller, is also observed when the G is at any of the following positions:

```
Position +2
Probe       5' (F)XXXXXXXXXXXX   or   5' XXXXXXXXXXXX(F)
               ||||||||||||             ||||||||||||
Target      3'XXXXXGXXXXXXXXXXXXXX   3' XXXXXXXXXXXXXXXGXXXX Position 0
Probe       5' (F)XXXXXXXXXXXX   or   5' XXXXXXXXXXXX(F)
               ||||||||||||             ||||||||||||
Target      3' XXXXXGXXXXXXXXXXXXXX  3' XXXXXXXXXXXXXXXGXXXX
``` whereas, single G residues in position +3 and position −1 shown below have little effect on detected fluorescence.

```
Position -1
Probe       5' (F)XXXXXXXXXXXX       or   5' XXXXXXXXXXXX(F)
               ||||||||||||                 ||||||||||||
Target      3'XXXXXGXXXXXXXXXXXX       3' XXXXXXXXXXXXXXXGXXXX Position +3
Probe       5' (F)XXXXXXXXXXXX       or   5' XXXXXXXXXXXX(F)
               ||||||||||||                 ||||||||||||
Target      3'XXGXXXXXXXXXXXXXXX         3'XXXXXXXXXXXXXXXXXXGXX
```

Small fluorescent change has also been noted when the G residue is in position +4.

When there is more than one G on the target strand, multiple G residues in any of the positions 0, +1, +2, +3, and +4 are effective to alter detected fluorescence. These are the "assigned positions." While the above representations of the assigned positions are shown with respect to G residues, the same terminology for the assigned positions is used throughout this specification with respect to other embodiments.

An alternative embodiment incorporates a "virtual nucleotide," in which the fluorescent dye itself is substituted for the base. In this embodiment the fluorescent entity has direct access to a guanine residue located at the complementary position (position 0) on the target strand. Fluorescent change may also be possible if the G is at +1 in either the 5' or 3' direction. Bases other than G in position 0 may also be useful for fluorescent change, depending on the fluorescent dye used to create the virtual nucleotide. For example, when fluorescein is used as the virtual nucleotide and an A residue is in position 0, an increase in fluorescence may be seen upon hybridization. The virtual nucleotide may be the end base or occupy an internal position of the oligonucleotide.

In another embodiment of this invention a probe with a label attached to the G residue can be used to facilitate fluorescence change upon duplex formation and dissociation. When fluorescein and fluorescein derivatives are used in this embodiment, the G to which the fluorescein is attached will itself effect quenching of the label when the probe is unbound and free. Upon formation of the probe-target duplex, the fluorescein becomes sterically sequestered from the G to which it is attached, dequenching will result, and fluorescence will be restored. A similar result is expected when the fluorophore is attached to the G residue, and a mismatching A or T is in the 0 position. In this embodiment best results have been obtained when there are no G residues in the −1 or +1 positions.

In a similar embodiment, the fluorescent entity may be attached to a residue via a flexible linker. When the residue is an A or T residue, one would expect increased fluorescence upon hybridization. Such a probe may be constructed using a C6dT nucleotide (Glen Research, Sterling, Va.) to provide the suitable flexibility. This construction would be appropriate for use for both target sequence detection and mutation detection. With mutation detection, the fluorescent entity should be located sufficiently removed from the mutation so that the mismatch does not affect the steric relationship between the fluorescent entity and the base to which the fluorophore is linked.

A wide variety of fluorophores can be used as labels for probes in this invention. Such groups include fluorescein and its derivatives, including but not limited to JOE, FAM, rhodamines, Alexa Fluor 488, Oregon Green dyes, erythrosins, and eosins, fluorescein-cyanine conjugates, such as Big Dyes, and derivatives of the bispyrromethene boron-difluoride dyes, such as BODIPY. When these dyes are attached to oligonucleotide probes, fluorescence is usually quenched upon annealing of the probe with its complementary target strand if the target has G residues in the assigned position(s). However, as discussed above, in another embodiment of this invention the direction of fluorescence change may be reversed by attaching the fluorophore to a G residue on the probe, preferably wherein there is an absence of other Gs at assigned positions on the complementary strand.

Similarly, in another embodiment of this invention, a fluorescent increase is seen if the fluorophore is attached to a "base analog" such as 5-nitroindole 2'-deoxynucleoside. In general, base analogs such as 5-nitroindole, 4-nitroindole, 6-nitroindole, and 3-nitropyrrole deoxynucleosides that form relatively stable pairing with normal bases are also useful. Other base analogs such as inosine, 5-iodo-2'-cytidine, and nebularine deoxynucleosides form weak base-pairing with the normal bases, and generally require the absence of the G residue at position +1 for a fluorescence change to be observed upon duplex formation and dissociation.

In yet another embodiment of this invention, fluorophores from the group of cyanine dimers and monomers, such as TOTO, YOYO, TO-PRO, Cy3, Cy5, Cy5.5, Cy7 etc., or dyes such as LCRed 705 may be used as the fluorescent dye. It has been found that probes incorporating these fluorescent dyes exhibit fluorescence augmentation rather than quenching upon probe hybridization.

Kits of the invention contain probes labeled with a single fluorescent dye. The kits may be used to detect the presence or absence of specific nucleic acid sequences in a sample, or may be used during or after the target is prepared by an amplification process such as PCR. Multiple probes may be multiplexed by Tm, color, or by direction of change in fluorescence. Detection of multicolor reporter signals could be achieved by single-wavelength excitation or by multiple wavelength excitation. The kits may further be used for quantitative analysis of the initial concentration of analyte.

Target amplification methods of the present invention include suitable procedures known in the art for amplifying a nucleic acid, provided that the method generates one or more target nucleic acid sequences capable of hybridizing to an oligonucleotide probe. Such suitable procedures include polymerase chain reaction (PCR); strand displacement amplification (SDA); nucleic acid sequence-based amplification (NASBA); cascade rolling circle amplification (CRCA), Q beta replicase mediated amplification; isothermal and chimeric primer-initiated amplification of nucleic acids (ICAN); transcription-mediated amplification (TMA), and the like. Therefore, when the term PCR is used, it should be understood to include other alternative amplification methods.

Analysis may occur during amplification in a homogeneous assay system. See, e.g., U.S. Pat. No. 6,174,670. Alternatively, the target nucleic acid may be studied through melting curve analysis subsequent to amplification. Other end-point analysis is also within the scope of this invention, and includes use of probes that are immobilized or are used with non-fluorescent tags, such as biotin. It is also understood that nucleic acid analysis independent of amplification is within the scope of this invention. When a probe of this invention is used in a homogeneous assay with PCR, the probe may be complementary to a locus located between the primers. Alternatively, the probe itself may function as one of the primers.

Rapid and specific detection of pathogens can be performed using single-labeled probes in real-time PCR and in post-PCR melting analysis. Pathogens include, but not limited to, Salmonella, pathogenic *E. coli* (such as *E. coli* O157:H7), *Listeria monocytogenes, Staphylococcus aureus,* Vibrio Cholerae, and *Clostridium botulinum.* Specimens applicable to PCR may include food samples, feces, tissue homogenate, washing fluid, and others. Single-labeled probes may also be used in mutation detection. Examples of mutations include, but are not limited to Factor V Leiden, hemoglobin C and S mutations, the thermolabile mutation of methylenetetrahydrofolate reductase, Factor II (prothrombin) G20210A mutation, hemochromatosis-associated mutations C187G and G845A, and the cystic fibrosis F508del mutation. It is understood that these lists are exemplary only, and they are not meant to be exhaustive.

EXAMPLE 1

Exemplary Single-Labeled Probes and Target Sequences for Guanine Quenching

The following are examples of probes that may be used for detection of a target sequence or mutation detection. Examples of primers for use with PCR amplification are also provided.

For Salmonella detection, a DNA fragment from the gene SpaQ (GenBank Accsession # U29364) may be amplified by PCR using, for instance, primers SQF (5'TGGATGATTTAGTGTTTGC (SEQ ID NO:1)), and SQR (5'CGCCCGTAAGAGAGTAAAAC (SEQ ID NO:2)), various probes may be used to detect amplification. Examples include:

```
SQP1  5'CCAAAAGGCAGCGTCTGTTCC    (SEQ ID NO:3)
SQP2  5'CCAAAAGGCAGCGTCTGTTC     (SEQ ID NO:4)
SQP3  5'CAAAAGGCAGCGTCTGTTCC     (SEQ ID NO:5)
SQP4  5'CCAAAAGGCAGCGTCTGTT      (SEQ ID NO:6)
SQP5  5'CAAAAGGCAGCGTCTGTT       (SEQ ID NO:7)
SQP6  5'AAAAGGCAGCGTCTGTTC       (SEQ ID NO:8)
SQP7  5'AAAAGGCAGCGTCTGTTCC      (SEQ ID NO:9)
SQP8  5'AAAAGGCAGCGTCTGTT        (SEQ ID NO:10)
``` where the fluorescent label is attached either to the 3' or 5' end of the probe. The 5'-labeled probes may be blocked from extension by the addition of a 3' phosphate. The above probes hybridize to one of the following target sequences

```
SQT1  5'AGGAACAGACGCTGCCTTTTGGC  (SEQ ID NO:11)
SQT2  5'AGGAACAGACGCTACCTTTTGGC  (SEQ ID NO:12)
SQT3  5'AGGAACAAACGCTACCTTTTGGC  (SEQ ID NO:13)
``` which is contained in the segment amplified by the primers. These designs provide G residues at positions −1 and 0, 0 and +1, or at +1 and +2 on the target strand depending on which probe is used. Fluorescence quenching or augmentation, depending on the specific fluorescent label used, may be observed by dissociation of the probe-target duplex. High selectivity and sensitivity is achieved in the detection of Salmonella subspecies using melting curve analysis. Melting curve analysis may be performed during or subsequent to PCR amplification.

Genotyping for Factor V Leiden (G1691A) mutation may be performed by PCR melting analysis by use of a single-labeled probe such as:

```
FVP1  5'CTGTATTCCTCGCCTGTC       (SEQ ID NO:14)
FVP2  5'TGTATTCCTCGCCTGTC        (SEQ ID NO:15)
FVP3  5'CTGTATTCCTCGCCTGT        (SEQ ID NO:16)
```

The probe may be labeled either at the 5' end (preferably with addition of a 3' phosphate) or at the 3' end. These probes may be used to hybridize to a segment of the Factor V gene (Genbank Accession #L32764) having the sequence of either

```
FVT1 5'TGGACAGGCGAGGAATACAGGT   (SEQ ID NO:17)
          (wild type)

FVT2 5'TGGACAGGCAAGGAATACAGGT   (SEQ ID NO:18)
          (Leiden mutant)
``` or a variant of either FVT1 or FVT2 with at least about 80% homology. Hybridization of probe to target will provide G residues either at positions 0 and +1, or at +1 and +2 on the target strand. The fragment containing the target sequences of the Factor V gene may be amplified by primers such as FVF (5'GAGAGACATCGCCTCTGGGCTA (SEQ ID NO:19)) and FVR (5'TGTTATCACACTGGTGCTAA (SEQ ID NO:20)). The Factor V Leiden mutation (a C:A mismatch) is distinguished from the normal type because of duplex destabilization leading to a decrease in Tm, detectable during melting analysis.

Genotyping of hemoglobin C (HbC) and S (HbS) mutations (Genbank Accession #U01317) may be performed by post PCR melting analysis with a single-labeled probe such as:

```
BGP1 5'CTGACTCCTGTGGAGAAGTCTG   (SEQ ID NO:21)

BGP2 5'TGACTCCTGTGGAGAAGTCTG    (SEQ ID NO:22)
```

The probe may be labeled either at the 5' end (with addition of a 3' phosphate) or at the 3' end. These probes hybridize to a target sequence of either

```
BGT1 5'CGGCAGACTTCTCCTCAGGAGTCAGGT   (SEQ ID NO 23)
          (wild type)

BGT2 5'CGGCAGACTTCTCCACAGGAGTCAGGT   (SEQ ID NO:24)
          (HbS mutant)

BGT3 5'CGGCAGACTTCTCCTTAGGAGTCAGGT   (SEQ ID NO:25)
          (HbC mutant)
``` or a variant of BGT1, BGT2, or BGT3 with 80% homology. Probe-target hybridization provides G residues at positions 0 and +1, or at +1 and +2 on the target strand. The fragment containing the mutations may be amplified by primers such as BGF (5'ACACAACTGTGTTCACTAGC (SEQ ID NO:26)) and BGR 5'CAACTTCATCCACGTTCACC (SEQ ID NO:27)). The HbS (complete match) and HbC genotypes (continuous G:T and T:T mismatches) can be discriminated from wild type (T:T mismatch) by differences in Tm.

Genotyping of the thermolabile mutation of methylenetetrahydrofolate reductase (Genbank Accession #U09806) may be performed by melting analysis with a single-labeled probe selected from the group consisting of:

```
MFP1 5'TGCGTGATGATGAAATCGGCTCC    (SEQ ID NO:28)

MFP2 5'TGCGTGATGATGAAATCGGCTC     (SEQ ID NO:29)

MFP3 5'TGCGTGATGATGAAATCGGCT      (SEQ ID NO:30)
```

The probe may be labeled either at the 5' end (with addition of a 3' phosphate) or at the 3' end. These probes will hybridize to target sequences of either

```
MFT1 5'CGGGAGCCGATTTCATCATCACGCAGC   (SEQ ID NO:31)
          (wild type)
```

-continued
```
MFT2 5'CGGGAGTCGATTTCATCATCACGCAGC   (SEQ ID NO:32)
          (mutant)
``` or their variants with at least about 80% homology. Probe-target hybridization will provide a G at position +1 for the 5'-labeled probes, or G residues at positions 0 and +1, 0, +1 and +2, or +1, +2, and +3 for 3'-labeled probes. The fragment of the methylenetetrahydrofolate reductase may be amplified by primers such as MFF (5'TGAAGGAGAAGGTGTCTGCGGGA (SEQ ID NO:33)) and MFR (5'AGGACGGTGCGGTGAGAGTG (SEQ ID NO:34)). The mutation results in the most stable G:T mismatch, but it can be distinguished by the destabilization of the duplex, particularly in post amplification melting analysis.

Genotyping of the Factor II (or prothrombin) G20210A mutation (Genbank Accession #M17262 and M33691) may be performed by post PCR melting analysis with a single-labeled probe such as F2P 5'TCTCAGCAAGCCTCAAT-GCT (SEQ ID NO:35). The probe may be labeled either at the 5' end (with addition of a 3'phosphate) or at the 3' end. The probe may be used to hybridize to target sequences of either

```
F2T1 5'GGGAGCATTGAGGCTCGCTGAGAGT    (SEQ ID NO:36)

(wild type)

F2T2 5'GGGAGCATTGAGGCTTGCTGAGAGT    (SEQ ID NO:37)
          (mutant)
``` or their variant with at least about 80% homology. Probe-target hybridization provides a G residue on the target strand at position +1 when the probe is 5'-labeled, and at positions +1, +2, and +3 when the probe is 3'-labeled. The fragment containing the mutation site may be amplified by primers such as F2F (5'ATTGATCAGTTTGGAGAGTAGGGG (SEQ ID NO:38)) and F2F (5'GAGCTGCCCATGAATAGCACT (SEQ ID NO:39)). The wild type duplex has a C:A mismatch and is distinguished from the mutation due to destabilization of the duplex.

Genotyping of the hemochromatosis-associated mutation C187G (Genbank Accession #Z92910) may be performed by melting analysis using a single-labeled probes such as:

```
HHDP1 5'CACACGGCGACTCTCATCATCATAGAAC   (SEQ ID NO:40)

HHDP2 5'ACACGGCGACTCTCATCATCATAGAAC    (SEQ ID NO:41)

HHDP3 5'CACACGGCGACTCTCATCATCATAGAA    (SEQ ID NO:42)
```

The probe may be labeled either at the 5' end (with addition of a 3' phosphate) or at the 3' end. These probes will hybridize to target sequences of either

```
HHDT1 5'  TGTTCTATGATCATGAGAGTCGCCGTGTGGA   (SEQ ID
            (wild type)                       NO:43)

HHDT2 5'  TGTTCTATGATGATGAGAGTCGCCGTGTGGA   (SEQ ID
            mutant)                           NO:44)
``` or a variant with at least about 80% homology. Probe-target hybridization provides G residues on the target strand at positions 0 and +1, or +1 and +2 for the 5'-labeled probes, and a G at position 0 or +1 for 3'-labeled probes. The fragment containing the mutation site is amplified by primers such as HHDF (5'CACATGGTTAAGGCCTGTTG (SEQ ID NO:45)) and HHDR (5'GATCCCACCCTTTCAGACTC (SEQ ID NO:46)). The mutation can be distinguished from wild type, wild type having has a C:C mismatch and a lower Tm.

Genotyping of the hemochromatosis-associated mutation G845A (Genbank Accession #Z92910) may be performed by post PCR melting analysis using single-labeled probes such as:

HCYP1 5'CACCTGGCACGTATATCTCTG     (SEQ ID NO:47)

HCYP2 5'ACCTGGCACGTATATCTCTG      (SEQ ID NO:48)

These probes may be labeled either at the 5' end (with addition of a 3' phosphate) or at the 3' end. These probes will hybridize to target sequences of either HCYT1 5'AGCAGAGATATACGTGCCAGGTGGA (SEQ ID NO:49)
       (wild type)

HCYT2 5'AGCAGAGATATACGTACCAGGTGGA (SEQ ID NO:50)
       (mutant)

or a variant with at least about 80% homology. Probe-target hybridization provides G residues on the target strand at positions 0 and +1, or +1 and +2 for the 5'-labeled probes, and a G at position +1 for 3'-labeled probes. The fragment containing the mutation site is amplified by primers such as HCYF (5'TGGCAAGGGTAAACAGATCC (SEQ ID NO:51)) and HCYR (5'TACCTCCTCAGGCACTCCTC (SEQ ID NO:52)). The mutation (C:A mismatch) can be distinguished from wild type by its lower Tm.

Genotyping of the common 3 base pair deletion (F508del) associated with cystic fibrosis may be detected with a single-labeled probe selected from the group consisting of:

CFP1 5'ATAGGAAACACCAAAGATGATATTTTC (SEQ ID NO:53)

CFP2 5'ATAGGAAACACCAAAGATGATATTTT  (SEQ ID NO:54)

The probe may be labeled either at the 5' end (with addition of a 3' phosphate) or at the 3' end, and hybridizes to target sequences of either CFT1 5'AGAAAATATCATCTTTGGTGTTTCCTATGA (SEQ ID NO:55)
       (wild type)

CFT2 5'AGAAAATATCATTGGTGTTTCCTATGA   (SEQ ID NO:56)
       (deletion mutation)

or their variant with at least about 80% homology. Probe-target hybridization provides a G on the target strand at position +1 with the 5' label, and a G at position 0 or +1 with the 3' label. The fragment containing the mutation site (Genbank Accession # M55115) may be amplified by primers such as CFF (5'GGAGGCAAGTGAATCCTGAG (SEQ ID NO:57)) and CFR (5'CCTCTTCTAGTTGGCATGCT (SEQ ID NO:58)). The mutation results in the destabilization of the duplex and a corresponding decrease in the Tm.

In all of the above examples, the fluorescent entity is provided on the '5 or '3 end nucleotide, with at least one G located in the 0, +1, or +2 position on the target strand. It is understood that the fluorescent entity may be located on a nucleotide internal to the end of the oligonucleotide probe, if the fluorescent entity has sufficient access to a G residue. For example, given appropriate linker structure, as is known in the art, the fluorescent entity may be linked one base internal to the end, and fluorescence maybe quenched by a G residue located at positions +1, 0, or −1 (relative to the position of the fluorescent entity). Other constructs wherein the linker is sufficiently flexible to allow access of the fluorescent entity to a G residue are considered to be within the scope of this invention.

EXAMPLE 2

Probe-Target Dissociation Monitored by 3'-Labeled Probes

DNA oligonucleotides shown in Table 1 were prepared by standard DNA synthesis using solid-phase phosphoramidite chemistry with conventional deprotection, followed by desalting and purification steps using a Sephadex G-25 column and $C_8$-reversed-phase HPLC. The probe oligonucleotides were labeled at the 3' end with a fluorescein molecule (a 5-carboxyfluorescein moiety with a $C_6$ cyclic linker) by use of fluorescein CPG column supports (Catalog number BGX-6190-1, BioGenex Inc, San Ramon, Calif.).

Figure 2:
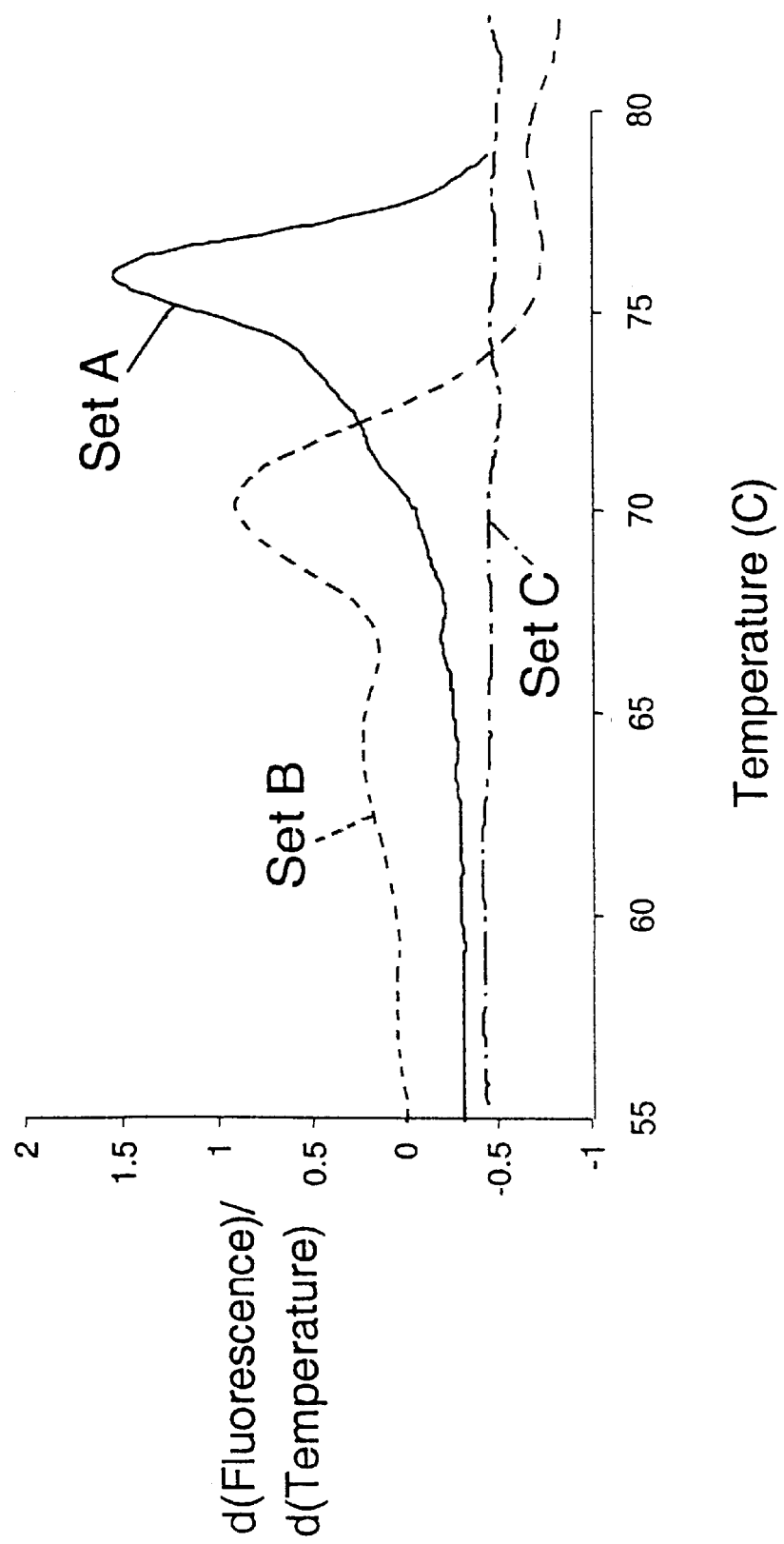
FIG. 2. is a dF/dT plot of the data shown in FIG. 1, with the melting curves converted to melting peaks.

A real-time rapid PCR thermal cycler apparatus (LightCycler instrument, Roche Molecular Biochemicals, Indianapolis, Ind.) was used to monitor changes in fluorescence emission during denaturation (or dissociation) of the probe from target. The samples consisted of 0.1 $\mu$M of probe oligonucleotide, 0.12 $\mu$M or 0.24 $\mu$M of target, 5 mM $MgCl_2$, 0.25 mg/ml bovine serum albumin (BSA), and 50 mM Tris buffer (pre-set crystals, pH 8.3 at 25° C.). Samples were first denatured at 95° C. and cooled quickly to ensure annealing of probe to target. Then fluorescence emission intensity was measured as the temperature was changed from 40° C. to 97° C. at a heating ramp of 0.2° C./sec. Samples were excited at 470 nm. Fluorescence emission was detected with a 20 nm band-pass filter centered at 530 nm using the step-acquisition mode of the instrument. For Sets A and B, an increase in fluorescence was observed as the temperature increased and transitioned through the melting temperature (Tm) of the probe (76° C. for Set A, and 66° C. for Set B)(FIG. 1). The degree of increase in fluorescence was greater with the higher amount of target. Change in fluorescence is further clarified by plotting the first derivative of the fluorescence data against temperature (FIG. 2). Set C showed very little, if any, change in fluorescence intensity.

TABLE 1

| General oligonucleotide constructs (only the bases near the fluorescent label are shown) | Guanine position on target strand | Fluorescence change upon dissociation of probe from target |
|---|---|---|
| Set A | | |
| Probe (35 ntd) 5'---ACCAC(F)3' | 0, +3 | Increase |
| Target(55 ntd) 3'---TGGTGCTGG---5' | | |

TABLE 1-continued

| General oligonucleotide constructs (only the bases near the fluorescent label are shown) | Guanine position on target strand | Fluorescence change upon dissociation of probe from target |
|---|---|---|
| Set B | | |
| Probe (27 ntd) 5'---AAGGG(F)3' | +1 | Increase |
| Target(35 ntd) 3'---TTCCCGTCCG---5' (SEQ ID NO:60) | | |
| Set C | | |
| Probe (15 ntd) 5'---TAGCG(F)3' | -1 | No change |
| Target(23 ntd) 3'---ATCGCACAGC---5' (SEQ ID NO:61) | | |

Number of nucleotides (ntd); Carboxyfluorescein (F)

EXAMPLE 3

Effect of Base Analogs on Fluorescent Signal

The G residue on the 3' end of the probe described in Set B (Example 2) was substituted with various base analogs shown in Table 2. Base analogs were obtained as phosphoramidites (Glen Research, Sterling, Va.) and incorporated into the oligonucleotides during DNA synthesis. Change in fluorescence intensity as the probe dissociated from the target was measured as in Example 2. Fluorescence change upon hybridization of probe to target was measured by a fluorimeter. Each sample contained 0.1 $\mu$M of probe, and 0.12 $\mu$M of target. There was very little change in the emission wavelength of fluorescein upon probe-target annealing. The samples with base analogs 5-nitroindole and 5-iodo-2'-cytidine deoxynucleosides showed fluorescence increase upon probe-target hybridization, and fluorescence decrease after probe dissociation from target. When the G at position +1 was changed to T on the target strand, increased fluorescence signal upon hybridization and fluorescence quenching upon probe dissociation were observed with these and other base analogs, except for 6-methoxyaminopurine, which generated no change in fluorescence. The direction of fluorescent change was opposite of that of the original G residue (Table 2).

TABLE 2

| | | | Fluorescence Change | |
|---|---|---|---|---|
| Set | Base substitution at 3' end of probe | G at position +1 on target strand | hybridization of probe to target | dissociation of probe from target |
| B | Guanine (no substitution) | Yes | Decrease | Increase |
| B' | | No | Increase | Decrease |
| D | Nebularine | Yes | None | None |
| D' | | No | Increase | Decrease |
| E | Inosine | Yes | None | None |
| E' | | No | Increase | Decrease |
| F | 5-nitroindole | Yes | Increase | Decrease |
| F' | | No | Increase | Decrease |
| G | 3-nitropyrrole | Yes | None | None |
| G' | | No | Increase | Decrease |
| H | 5-iodo-2'-cytidine | Yes | Slight Increase | Slight Decrease |
| H' | | No | Increase | Decrease |

TABLE 2-continued

| | | | Fluorescence Change | |
|---|---|---|---|---|
| Set | Base substitution at 3' end of probe | G at position +1 on target strand | hybridization of probe to target | dissociation of probe from target |
| I | 6-methoxy aminopurine | Yes | None | None |
| I' | | No | None | None |

EXAMPLE 4

Probe-Target Dissociation Monitored by 5'-Labeled Probes: Position, and Dosage Effects of Guanines Oligonucleotides shown in Table 3 were obtained from Operon Technologies Inc (Alameda, Calif.). The probe oligonucleotides were 27 nucleotides in length and labeled at the 5' end with a 5-fluorescein molecule attached to a thiourea-linked $C_6$ alkyl chain, and blocked from extension with a 3-phosphate. Target oligonucleotides were complementary to probes except they had four additional overhanging nucleotides at the 3' end. Complementary pairs of probes (0.2 $\mu$M) and targets (0.4 $\mu$M) were annealed in the presence of 50 mM Tris, pH 8.3, 3 mM $MgCl_2$, and 250 $\mu$g/ml BSA, and heated at 0.1° C./sec to 90° C. with continuous fluorescence acquisition to observe the change in fluorescence intensity upon dissociation of probe. The percent change in fluorescence from probe dissociation was determined by extrapolation of the linear decrease in fluorescence measured above the melting transition to values below the melting transition. The results indicated that at least one G at positions 0, +1, or +2 on the target strand is needed for significant fluorescence change to occur upon probe-target dissociation. The magnitude of fluorescence change was maximized when G residues occupied all three positions. Position +3 was marginally effective. Similar results (not shown) demonstrate that a G residue at position +4 was also marginally effective. Position -1 had very little effect, if any, as was also the case when there were no G residues at positions -1 through +3 (Table 3).

TABLE 3

| Oligonucleotide constructs | | Guanine position on target | Fluorescence change upon dissociation of probe from target | Percent Change |
|---|---|---|---|---|
| Probe 1 | 5' (F)AAAGG---3' | | | |
| Probe 2 | 5' (F)ACAGG---3' | | | |
| Probe 3 | 5' (F) CAAGG---3' | | | |
| Target J | 3" AAAATTTCC---5' | None | Decrease | -3% |
| Target K | 3' AAAATGTCC---5' | -1 | Slight Increase | +0.3% |
| Target L | 3' AAAAGTTCC---5' | 0 | Increase | +12% |
| Target M | 3' AAAGTTTCC---5' | +1 | Increase | +25% |
| Target N | 3' AAGATTTCC---5' | +2 | Increase | +8% |
| Target O | 3' AGAATTTCC---5' | +3 | Increase | +4% |
| Target P | 3' AAGGTTTCC---5' | +1, +2 | Increase | +32% |
| Target Q | 3' AGGGTTTCC---5' | +1, +2, +3 | Increase | +37% |
| Target R | 3' AAAGGTTCC---5' | 0, +1 | Increase | +29% |
| Target S | 3' AAGGGTTCC---5' | 0, +1, +2 | Increase | +34% |
| Target T | 3' AGGGGTTCC--5' | 0, +1, +2, +3 | Increase | +38% |
| No target | | | Unchanged | 0% |

EXAMPLE 5

Probe-Target Dissociation Monitored by 5'-Labeled Probes: Effect of the Base Under the Label Oligonucleotides with the same core construct as described in Example 4 were prepared with minor changes in their sequences as shown in Table 4. These oligonucleotides were used to measure changes in fluorescence emission intensity upon probe-target dissociation as in Example 4. The results indicated that the presence of a G residue at position 0 on the target strand provides significant increase in fluorescence upon probe-target dissociation (Set W).

The C residue in position 0 caused the fluorescence change to occur in the opposite direction, i.e. the C residue interfered with quenching by the '5 labeled G residue and fluorescence signal was once again quenched upon the melting of the duplex (Table 4). However, this effect is best seen when there is an absence of G residues in the −1 or +1 positions.

TABLE 4

| Oligonucleotide constructs (base at position 0 is underlined) | Fluorescence change upon dissociation of probe from target | Percent Change |
|---|---|---|
| Set J  Probe 5' (F)AAAGG---3' | Slight decrease | -0.3% |
|        Target 3' AAAATTCC---5' | | |
| Set U  Probe 5' (F)TTAAGGA---3' | Slight increase | +0.5% |
|        Target 3' AAAAATCC---5' | | |
| Set V  Probe 5' (F)GGAGG---3' | Decrease | -16% |
|        Target 3' AAAACCTCC---5' | | |

TABLE 4-continued

| Oligonucleotide constructs (base at position 0 is underlined) | Fluorescence change upon dissociation of probe from target | Percent Change |
|---|---|---|
| Set W  Probe 5' (F)CCAGG---3' | Increase | +14% |
|        Target 3' AAAAGGTCC---5' | | |

EXAMPLE 6

Figure 3:
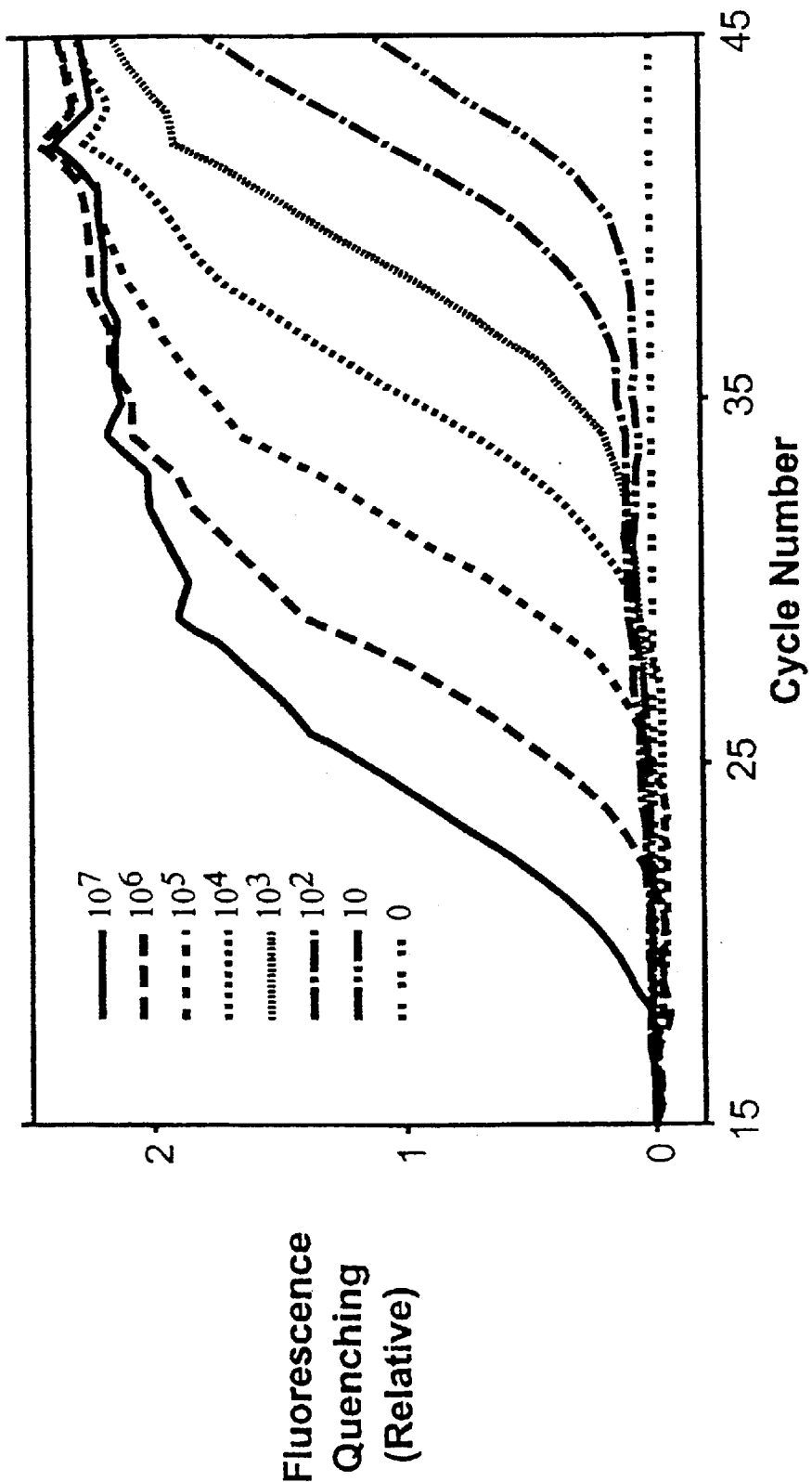
FIG. 3. is a plot of cycle number vs relative fluorescence quenching.

Monitoring Amplification and Quantification by Fluorescence Quenching Using 5'-Labeled Probes A 5'-fluorescein-labeled 27 nucleotide oligonucleotide probe 5'CCAGGAAAACATAGTAAAAAATGGAAT (SEQ ID NO:62) blocked at the 3'-end with phosphate was used to detect amplification of a fragment from the lipoprotein lipase gene (GenBank Accession #AF050163). The probe was positioned so that the target strand had G residues at position 0 and +1 relative to the fluorescein label. PCR reactions were carried out using 0.2 mM each of dATP, dGTP, dCTP, dTTP, 0.1 µM probe, 3 mM MgCl$_2$, KlenTaq polymerase (AB Peptides, St. Louis, Mo., 0.4 U/reaction), 50 mM Tris (pH 8.3, 25° C.), BSA (500 µg/ml). Primers were 5'GAATCGTGGTTTATCAAGTCATTAAAATCA (SEQ ID NO:63) (0.25 µM) and 5'GTGTTGATACTTGAA-CATTATTTAGCTACAA (SEQ ID NO:64) (0.5 µM). The starting template was purified PCR product at $10^7$, $10^6$, $10^5$, $10^4$, $10^3$, 100, 10, and 0 copies per reaction. Rapid cycle PCR with fluorescence monitoring was performed in 10 µl volumes using the LightCycler instrument. Amplification was performed by denaturation at 94° C., annealing at 50° C., a transition at 1° C./sec to 54° C., a transition at 3° C./sec to 74° C., and extension at 74° C. for 10 sec, producing a 169 bp product. Fluorescence was acquired once each cycle at 54° C. The amplification required 39 min for 45 cycles. FIG. 3 shows fluorescence data plotted as the relative amount of quenching beyond background vs cycle number. The original fluorescence data were adjusted by 1) inversion (taking the reciprocal of the fluorescence), 2) proportional background adjustment of each curve over the relevant cycle interval (LightCycler software), and 3) subtracting the no template control value from each sample at each cycle. The results indicated that the system can detect as little as one copy per reaction, and that reliable quantification of initial copies of template is possible.

EXAMPLE 7

Amplification, Detection, and Typing of Salmonella Strains with 3'-Labeled Probes Sixteen Salmonella serovars from the Salmonella Reference Collection C were obtained from the Salmonella Genetic Stock Centre, University of Calgary, Canada. These serovars (Centers for Disease Control and Prevention strain numbers: 151-85, 3472-64, 346-86, 409-85, 156-87, 678-94, 2584-68, 287-86, 750-72, 2703-76, 1363-65, 347-78, 2439-64, 5039-68 and strains S 6623, Institute Pasteur E88.374) represent a genetically diverse cross section of Salmonella as all seven subspecies of Salmonella enterica and Salmonella bongorii are represented. Five E. coli strains from the E. coli Reference Collection were also obtained as negative controls. The bacteria were cultured overnight in Luria Broth and the genomic DNA was purified using a template preparation kit (Roche Molecular Biochemicals, High Pure PCR Template Preparation kit). Oligonucleotide primers SQF (SEQ ID NO:1) and SQR (SEQ ID NO:2) were used to amplify the SpaQ gene. Probes SQP1 (SEQ ID NO:3), SQP2 (SEQ ID NO:4) and SQP3 (SEQ ID NO:5) were labeled at their 3' end with carboxyfluorescein, similar to the examples described in Example 2. Probe SQP8 (SEQ ID NO:10) was labeled at the 5' end with fluorescein, similar to the examples described in Example 4. PCR reactions were carried out as in Example 6, with the following exceptions: 0.5 $\mu$M primer SQF, 0.25 $\mu$M primer SQR, 0.6 mM dUTP in place of dTTP, 0.2 $\mu$M of one of the probes, 4 mM MgCl$_2$, the addition of TaqStart antibody (Clontech, Palo Alto, Calif., 10 ng/reaction), BSA (250 $\mu$g/ml) and 2 ng of each DNA per reaction. PCR with fluorescence monitoring was performed in 10 $\mu$l volumes in the LightCycler instrument. Amplification conditions were 94° C. (0 seconds, 20° C./second transition rate); 55° C. (10 seconds, 20° C./second transition rate); 74° C. (10 seconds, 2° C./second transition rate). Melting curve analysis was conducted at the end of 40 PCR cycles using a ramp rate of 0.2° C./second. All 16 Salmonella serovars were detected by the melting curve analysis that produced melting peaks at the appropriate Tms (64° C. and 54° C. for probe SQP1 (SEQ ID NO:3), and 62° C. and 52° C. for SQP2 (SEQ ID NO:4), 61° C. and 51° C. for probe SQP3 (SEQ ID NO:5), 60° C. and 50° C. for probe SQP8 (SEQ ID NO:10)), but none of the E. Coli species were detected. Salmonella subspecies IV and VI were easily differentiated from the other subspecies on the basis of a 10° C. shift in melting temperature of the probe-amplicon duplex.

EXAMPLE 8

Genotyping with 5'-Labeled Probes

For all of the following examples, PCR with fluorescence monitoring was performed as in Example 6, except each reaction contained 0.5 $\mu$M of each primer, 0.4 U of Taq polymerase (Roche Molecular Biochemicals, Indianapolis, Ind.) instead of KlenTaq polymerase, and 50 ng of purified genomic DNA. Temperature transition rates were programmed for 20° C./sec and holding times of 0 sec were used unless indicated otherwise. Melting curve analysis was performed by heating to 95° C., annealing at 40° C. for 60 sec, and melting at 0.1° C./sec to 80° C. with continuous acquisition of fluorescein fluorescence. Characteristic Tm shifts of all of the alleles presented here are summarized in Table 5. The Table also indicates that predictive tools can be used for single-labeled probes.

Factor V

Figure 4A:
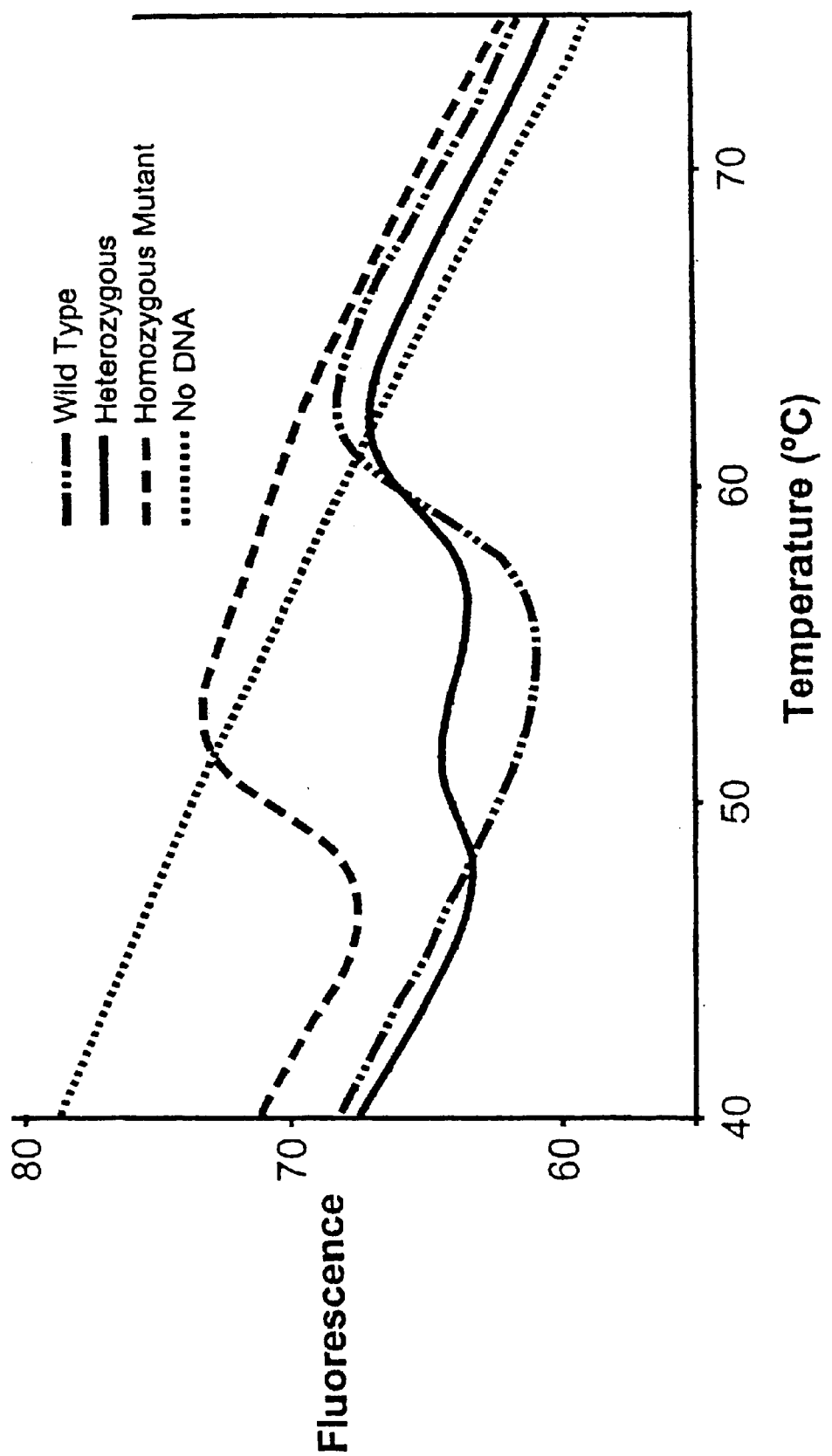
FIGS. 4A and B are plots of melting curve data for the Factor V gene.
Figure 4B:
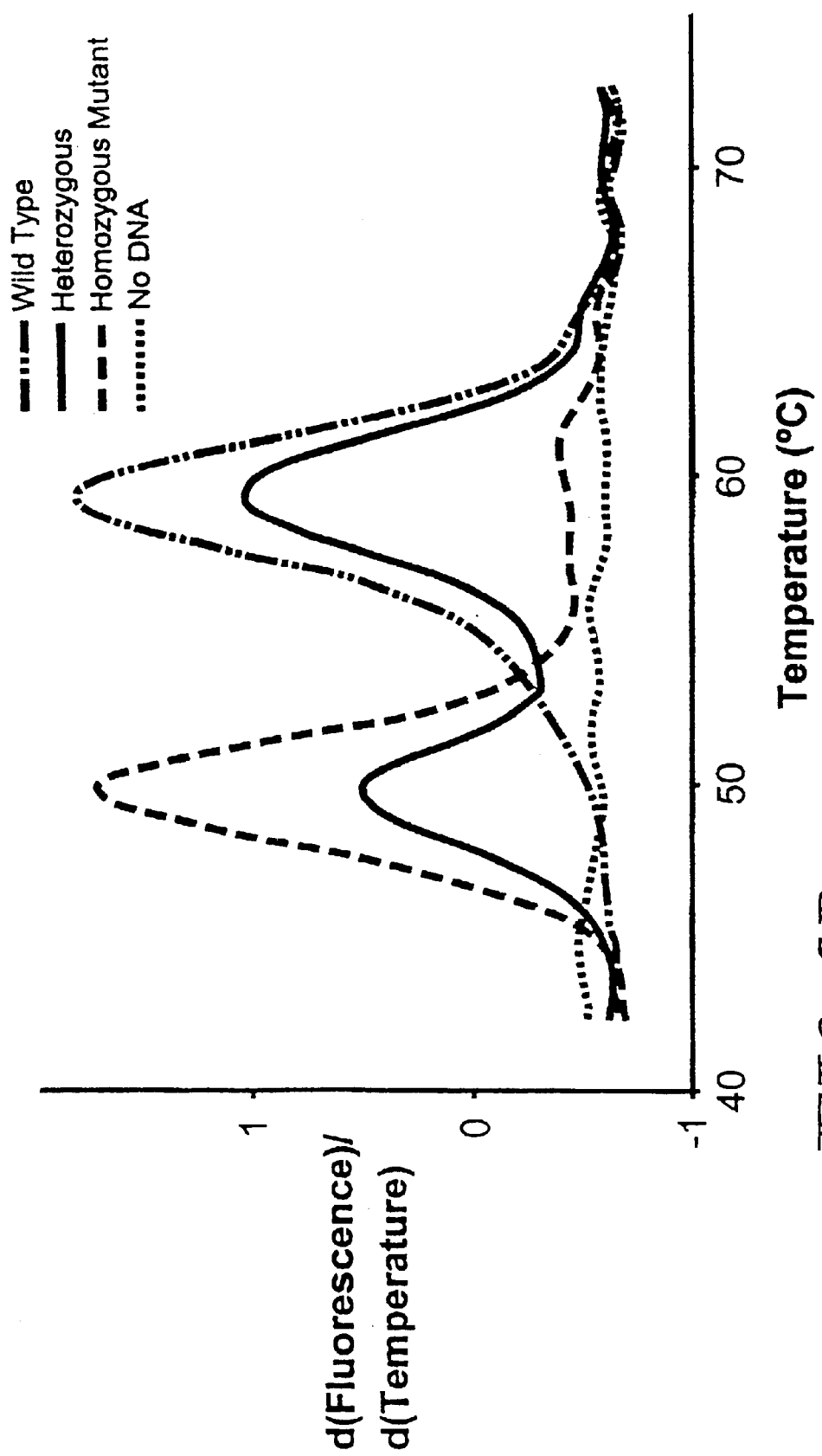

One hundred genomic DNA samples of unknown genotype for the factor V Leiden were obtained from clinical samples submitted to Associated Regional and University Pathologists (ARUP, Salt Lake City, Utah). The factor V locus was amplified using primers FVF (SEQ ID NO:19) and FVR (SEQ ID NO:20), and analyzed by the single-fluorescein 5'-labeled probe FVP1 (SEQ ID NO:14). Rapid cycle PCR was performed for 45 cycles of denaturation at 94° C., annealing at 50° C. for 10 sec, and a transition at 1° C./sec to 72° C., producing a 222 bp product. Melting curve analysis was automatically performed after PCR by heating to 94° C., annealing at 40° C. for 2 min, and melting at 0.1° C./sec to 75° C. with continuous acquisition of fluorescein fluorescence. The amplification required 41 min and the melting protocol, 9 min. Results were compared against those using conventional Hybridization probe assays with the donor-reporter dye combination (Lay et al, 1997. *Clinical Chemistry* 43:2262–2267). Concordance between the two methods was 100%. Eighty-seven wild-type samples, 12 heterozygous samples, and 1 homozygous mutant sample were identified by characteristic Tm shifts (FIG. 4).

Beta Globin

Rapid cycle PCR (primers BGF (SEQ ID NO:26) and BGR (SEQ ID NO:27)) was performed for 35 cycles of denaturation at 94° C., annealing at 50° C. for 10 sec, and a 1° C./sec transition to 70° C., producing a 110 bp product. Melting curve analysis with the 5'-fluorescein labeled probe BGP1 (SEQ ID NO:21) was performed after PCR by heating to 95° C., annealing at 40° C. for 30 sec, and melting at 0.1° C./sec to 80° C. with continuous acquisition of fluorescein fluorescence. The amplification required 35 min and the melting protocol, 9 min. The genotype of all 3 alleles (wild type, HbS, HbC) was identified by characteristic Tm shifts.

Methylenetetrahydrofolate Reductase

Rapid cycle PCR (primers MFF (SEQ ID NO:33) and MFR(SEQ ID NO:34)) was performed for 40 cycles of denaturation at 94° C. and annealing/extension at 60° C. for 20 sec, producing a 198 bp product. TaqStart™ antibody (88 ng) was added to each reaction. The amplification required 27 min and the melting protocol, 8 min. Genotyping was performed using a 5'-fluorescein-labeled primer MFP1 (SEQ ID NO:28). The genotype of wild and mutation was identified by characteristic Tm shifts.

Factor II (Prothrombin)

Rapid cycle PCR (primers F2F (SEQ ID NO:38) and F2R (SEQ ID NO:39)) was performed for 35 cycles of denaturation at 94° C., annealing at 58° C. for 15 sec, and a 1° C./sec transition to 72° C., producing a 154 bp product. Melting curve analysis was performed with a 5'-fluorescein-labeled probe F2P (SEQ ID NO:35). The amplification required 29 min and the melting protocol, 8 min. The mutation and wild type alleles were distinguished by characteristic Tm shifts.

Hereditary Hemochromatosis

Rapid cycle PCR (primers HHDF (SEQ ID NO:45) and HHDR (SEQ ID NO:46) for mutation C187G and primers HCYF and HCYR for mutation G845A) was performed for 35–50 cycles of denaturation at 94° C., annealing at 60° C. for 10 sec, and a 1° C./sec transition to 72° C. Melting curve analysis was performed with 5'-fluorescein-labeled probes HHDP1 (SEQ ID NO:40) for the C187G allele, and HCYP1 (SEQ ID NO:47) for the G845A allele. Wild type and mutant alleles were identified by characteristic Tm shifts.

Cystic Fibrosis

Rapid cycle PCR (primers CFF (SEQ ID NO:57) and CFR (SEQ ID NO:58)) was performed for 44 cycles of denaturation at 95° C. and annealing/extension at 60° C. for 20 sec, producing a 256 bp product. TaqStart antibody (88 ng) was added to each reaction. Melting analysis was performed using a 5'-fluorescein labeled primer CFP1 (SEQ ID NO:53). The amplification required 25 min and the melting protocol, 8 min. The deletion allele was differentiated from the wild type allele by its characteristic Tm shift.

TABLE 5

Measured and predicted Tms derived from single-labeled fluorescein probes.

| Gene | Genotype | Melting Temperature (° C.) | |
|---|---|---|---|
| | | Measured | Predicted |
| Factor V | Wild type | 59.5 | 58.4 |
| | G1691A | 50.0 | 47.0 |
| Hemoglobin | Wild type | 60.4 | 57.6 |
| | Hb S | 64.7 | 63.1 |
| | Hb C | 55.8 | N/A |
| MTHFR | Wild type | 66.9 | 66.8 |
| | C667T | 63.1 | 62.2 |
| Cystic Fibrosis | Wild type | 62.9 | 59.2 |
| | F508del | 53.2 | N/A |
| Factor II | Wild type | 55.0 | 50.7 |
| | G20210A | 62.5 | 58.7 |
| HFE-C282Y | Wild type | 63.3 | 61.3 |
| | C187G | 54.7 | 52.6 |
| HFE-H63D | Wild type | 63.3 | 61.3 |
| | G845A | 69.3 | 67.9 |

N/A: not available

EXAMPLE 9

Mutation Detection by Probe Multiplexing

Figure 5A:
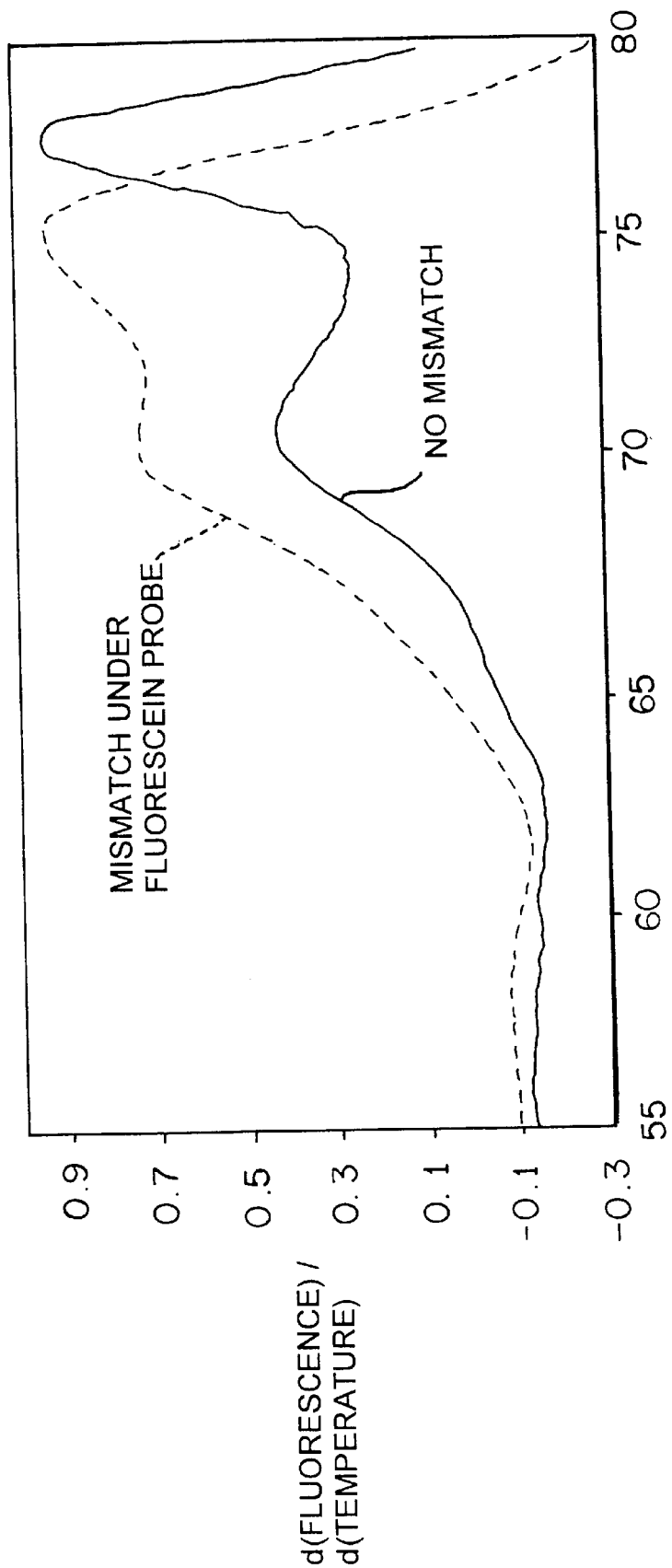
FIGS. 5A and B show melting curves for mutation analysis by probe multiplexing.
Figure 5B:
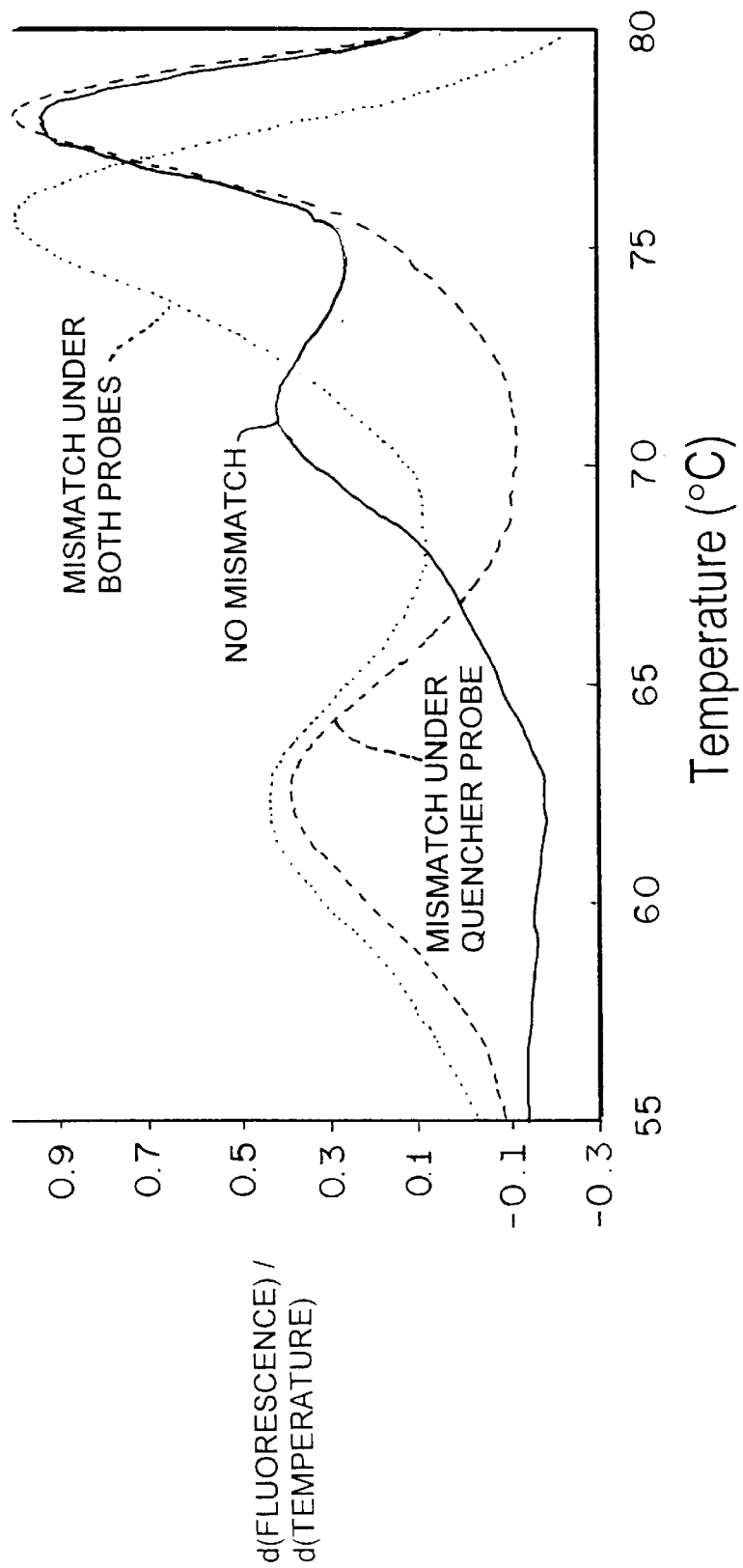
FIG. 5B shows no mismatch vs mismatch under quencher probe or under both probes.

A 3'-fluorescein labeled oligonucleotide probe Y 5'CTTGATGAGGATCCCAAAGACCACCCCCAAGACC AC(F) (SEQ ID NO:65), and a second oligonucleotide labeled at its 5' end with BlackHole quencher dye (BH1, BioSearch Technologies, Novato, Calif.) probe Z 5'(F) ACCAGCAGAATGCCAACCA (SEQ ID NO:66) were prepared. On the target strand, a G residue was located at position 0 relative to the fluorescein label. Four target oligonucleotides, 55 nucleotides in length, one completely complementary with both probes, a second with a single-base mismatch under probe Y (SEQ ID NO:65), the third with a single-base mismatch under probe Z (SEQ ID NO:66), and a fourth with single mismatches each under probe Y (SEQ ID NO:65) and probe Z (SEQ ID NO:66) were also prepared. The two probes were simultaneously hybridized to target, and melting analysis with fluorescence monitoring was performed as described in Example 2. An increase in fluorescence was observed as probe Z (SEQ ID NO:66)(with the quencher dye) dissociated from the template (Tm=70° C.), followed by another increase in fluorescence as the fluorescein-labeled probe Y (SEQ ID NO:65) dissociated (Tm=77.5° C.). The single-base mismatch under the fluorescein-labeled probe (FIG. 5A) as well as that under the quencher probe (FIG. 5B) were both detected by downward Tm shifts characteristic to each of the mismatches. The double-mismatch (i.e. one mismatch under each probe) was also unambiguously detected (FIG. 5B).

EXAMPLE 10

Comparison of Quenching and Dequenching Probes

Oligonucleotide probes (27 ntds) were synthesized with fluorescein, JOE, Cy5, and LCRed 705 dyes attached to their 5' end. A complementary strand of 38 ntds having two G residues at position 0 and +1 was also prepared. Probes were hybridized to the complementary strand, and fluorescence change was measured as the probe dissociated, as described in Example 4, except appropriate filters were used for excitation and emission detection. Percent change in fluorescence intensity was 28% for fluorescein, 20% for JOE, both indicating quenching by hybridization and dequenching by duplex dissociation, and −11% for Cy5, −12% for LCRed 705, indicating augmentation by hybridization and quenching by duplex dissociation.

EXAMPLE 11

Genotyping by Quenching/Augmentation of an Oligonucleotide Probe Internally Labeled with Fluorescein as a Virtual Nucleotide An oligonucleotide complementary to the factor V Leiden (G1691A) locus (Genbank Accession #L32764) was obtained from Operon (Alameda, Calif.) and used without further purification. A fluorescein-ON phosphoramidite (Clontech, Palo Alto, Calif.) was incorporated into the probe at the position complementary to the variable base and the probe was blocked from extension with a 3'-phosphate (FIG. 6). Hence, the fluorescein label is incorporated as a "virtual nucleotide" in the sequence CTGTATTCCTFGCCTGTCCAGG-P (SEQ ID NO:67). When hybridized to the factor V locus, the fluorescein is opposed to either a G or an A residue.

PCR with fluorescence monitoring was performed in 10 μl volumes in a rapid-cycle, real-time PCR instrument (LightCycler, Roche Molecular Biochemicals, Indianapolis, Ind.). The probe was included in the PCR amplification mixture with primers FVF (SEQ ID NO:19) (0.5 μM) and FVR (SEQ ID NO:20) (0.25 μM). Each reaction included the fluorescein-labeled probe at 0.1 μM, 200 μM of each dNTP (dATP, dCTP, dGTP, and dTTP), 50 mM Tris, pH 8.3 (25° C.), 3 mM MgCl$_2$, 500 μg/ml bovine serum albumin, 0.4 U of Taq polymerase (Roche Molecular Biochemicals), TaqStart antibody (88 ng, Clontech) and 50 ng of purified genomic DNA.

Genomic DNA of known genotypes were obtained from a prior study (Lay M J and C T Wittwer. *Clin. Chem.*43:12, 2262–2267, 1997). Rapid cycle PCR was performed for 45 cycles of denaturation at 95° C., annealing at 50° C. for 10 sec, and a transition at 1° C./sec to 72° C., producing a 222 bp product. Temperature transition rates not specified were programmed for 20° C./sec with holding times of 0 sec. Melting curve analysis was automatically performed after PCR by heating to 95° C., annealing at 40° C. for 30 sec, and melting at 0.1° C./sec to 75° C. with continuous acquisition of fluorescein fluorescence.

Fluorescent melting curve analysis used commercial LightCycler software except that the positive derivative of fluorescence with respect to temperature was plotted on the Y-axis instead of the negative derivative. The temperature interval used for polynomial estimation of the derivative was 8° C. and the digital filter was enabled.

The homozygous wild type genotype results in F:G oppositions, quenching of fluorescein fluorescence, and a Tm of 58.4° C., while the homozygous factor V Leiden genotype results in F:A oppositions and augmentation of fluorescence with a similar Tm. A heterozygote results in both F:G and F:A oppositions with an intermediate level of fluorescence. Note that genotyping is obtained by the direction of the change in fluorescence, not by characteristic Tms of each allele as in other examples. All genotypes can be clearly distinguished from each other.

Another example of use of a virtual nucleotide would be for detection of Salmonella with an analog of SEQ ID NO:3, 5'CCAAAAGGNAGCGTCTGTTCC (SEQ ID NO:59), wherein N is the fluorescent-label-containing virtual nucleotide, and quenching occurs upon hybridization when the virtual nucleotide is in close proximity to the G in the 0 position on the complementary strand.

EXAMPLE 12

Genotyping by Dequenching of an Oligonucleotide Probe with a Fluorescent Label on a G Residue PCR with fluorescence monitoring was performed as described in Example 11, but with the following changes: the Factor V locus was asymmetrically amplified using an 8:1 molar ratio of primer 5'AGAATAAATGTTATCA-CACTGGTGCTAA (SEQ ID NO:68, 0.5 µM) and primer 5'GACATCGCCTCTGGGCTA (SEQ ID NO:69, 0.06 µM); each reaction mixture included 200 mM Tris, pH 8.7 (25° C.), without TaqStart antibody, and 0.2 µM fluorescein-labeled probe 5'GGC<u>G</u>AGGAATACAGG(F) (SEQ ID NO:70) in which the underlined G is opposed to the Leiden mutation.

Rapid cycle PCR was performed with initial incubation at 95° C. for 5 s, followed by 45 to 60 cycles of denaturation (86° C.), annealing (55° C., 10 sec), and extension (using a transition rate of 1° C./s from 55° C. to 72° C.). This produced a 226 bp product from human DNA samples. Melting curve analysis was performed after PCR by heating to 95° C., cooling to 65° C., further cooling down to 30° C. at a rate of 0.25° C./s, and melting at a rate of 0.05° C./s to 65° C. with continuous acquisition of fluorescein fluorescence. Temperature transition rates were programmed at 20° C./s and holding times at 0 seconds unless otherwise specified. Fluorescent melting curve analysis was performed using the commercial LightCycler software with the conventional negative first derivative of fluorescence plotted against temperature.

Figure 7:
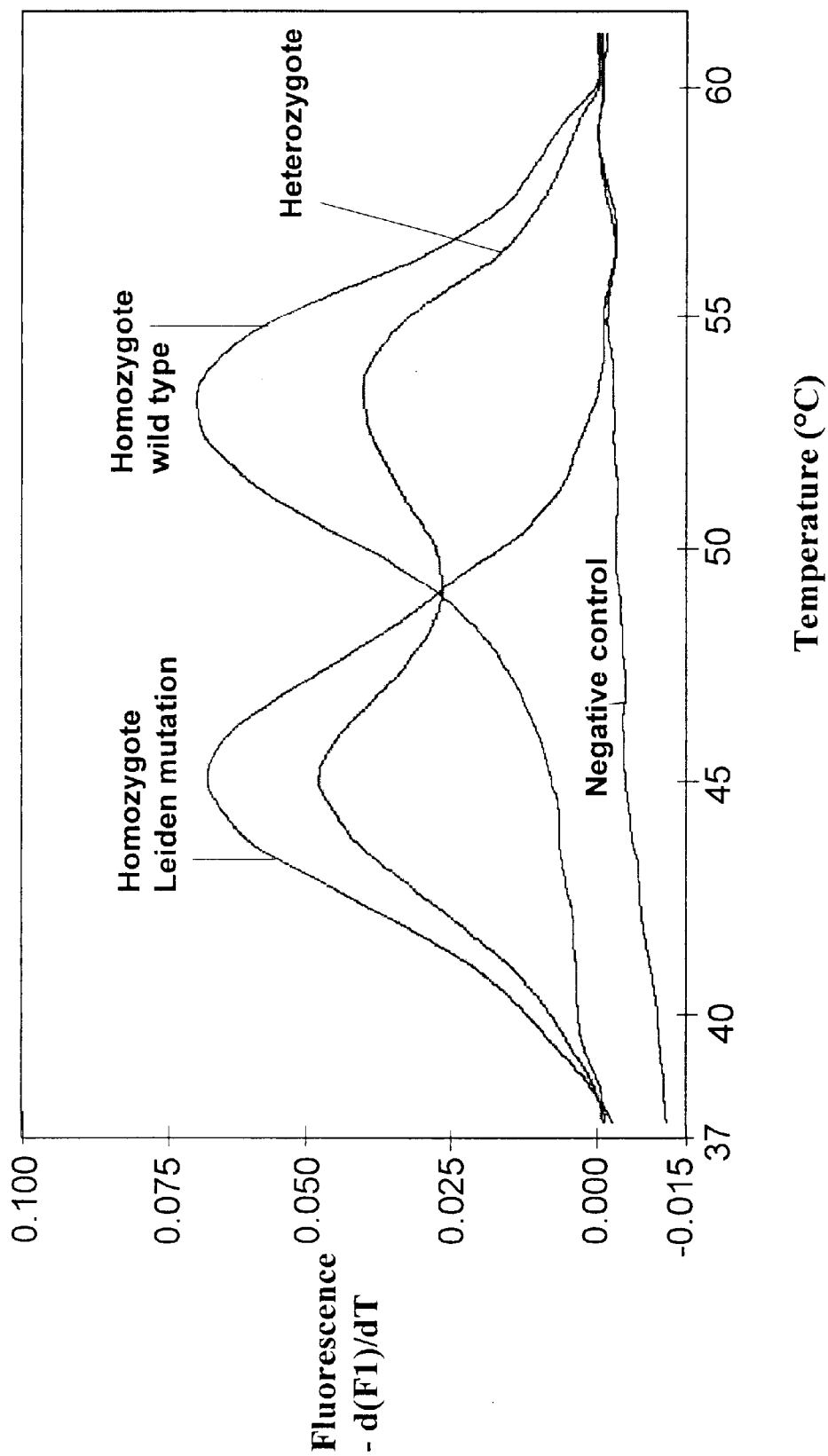
FIG. 7 shows homogeneous, real-time Factor V Leiden genotyping with a fluorescein dequenching probe. Melting curve data is presented as negative first derivative plots for homozygous wild type, homozygous mutant, heterozygous genotypes, and negative control.

Probe-target hybridization resulted in an increase in fluorescence. The homozygous wild type genotype (G:C match) had a Tm of 53° C., and was easily distinguished from the homozygous Factor V Leiden genotype (G:T mismatch) which had a lower Tm of 45° C. A heterozygote genotype showed both of the Tm values (FIG. 7).

Best results are obtained with asymmetric PCR, wherein the primer of the same sense as the probe is provided in smaller amounts than the opposite primer. When 45 cycles were performed, a 1:4 primer asymmetry produced the greatest signal. At 60 cycles, a 1:8 ratio was optimal. Compared to the 1:8 ratio, the dequenching peak area at a 1:16 ratio was 62%, at 1:4, 85%, and at 1:2, 37%. With this probe system, no signal was obtained when the primer concentrations were symmetric (equal).

EXAMPLE 13

Optimization of Quenching Probes

Figure 8A:
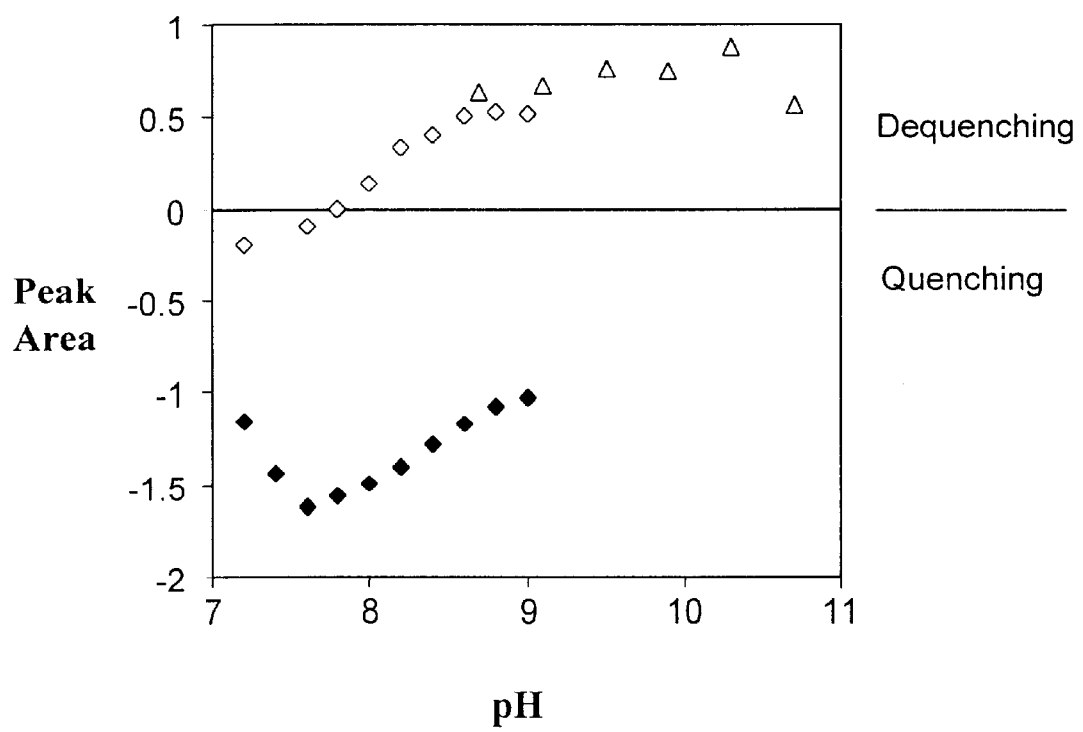
FIGS. 8a and 8b are plots of peak area obtained from melting curves vs either buffer pH (FIG. 8a), or cation concentration of buffer (8b). Data for the quenching probe (closed symbols) and for the dequenching probe (open symbols) are shown with buffer conditions of 10 mM Tris, 100–160 mM KCL (squares); 10 mM Tris pH8.3–8.8 (circles), and 10 mM 2-amino-2-methyl-1-propanol, 160 mM KCl (triangles).
Figure 8B:
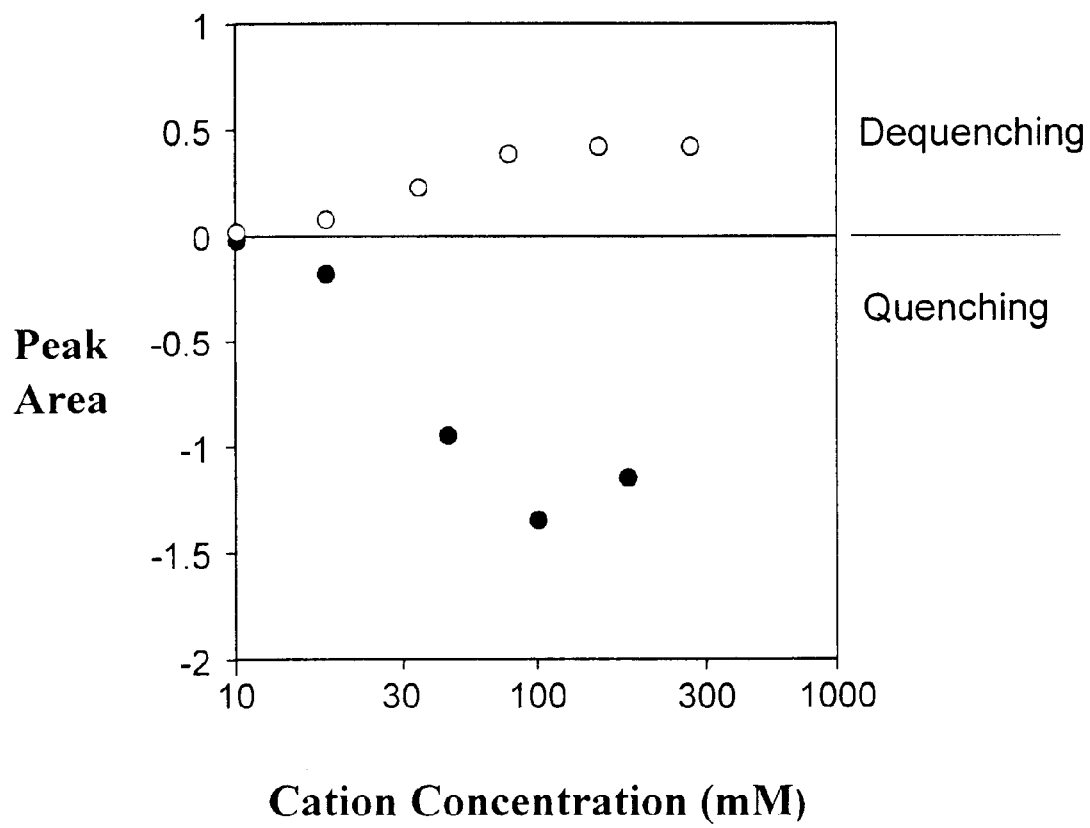
Figure 9:
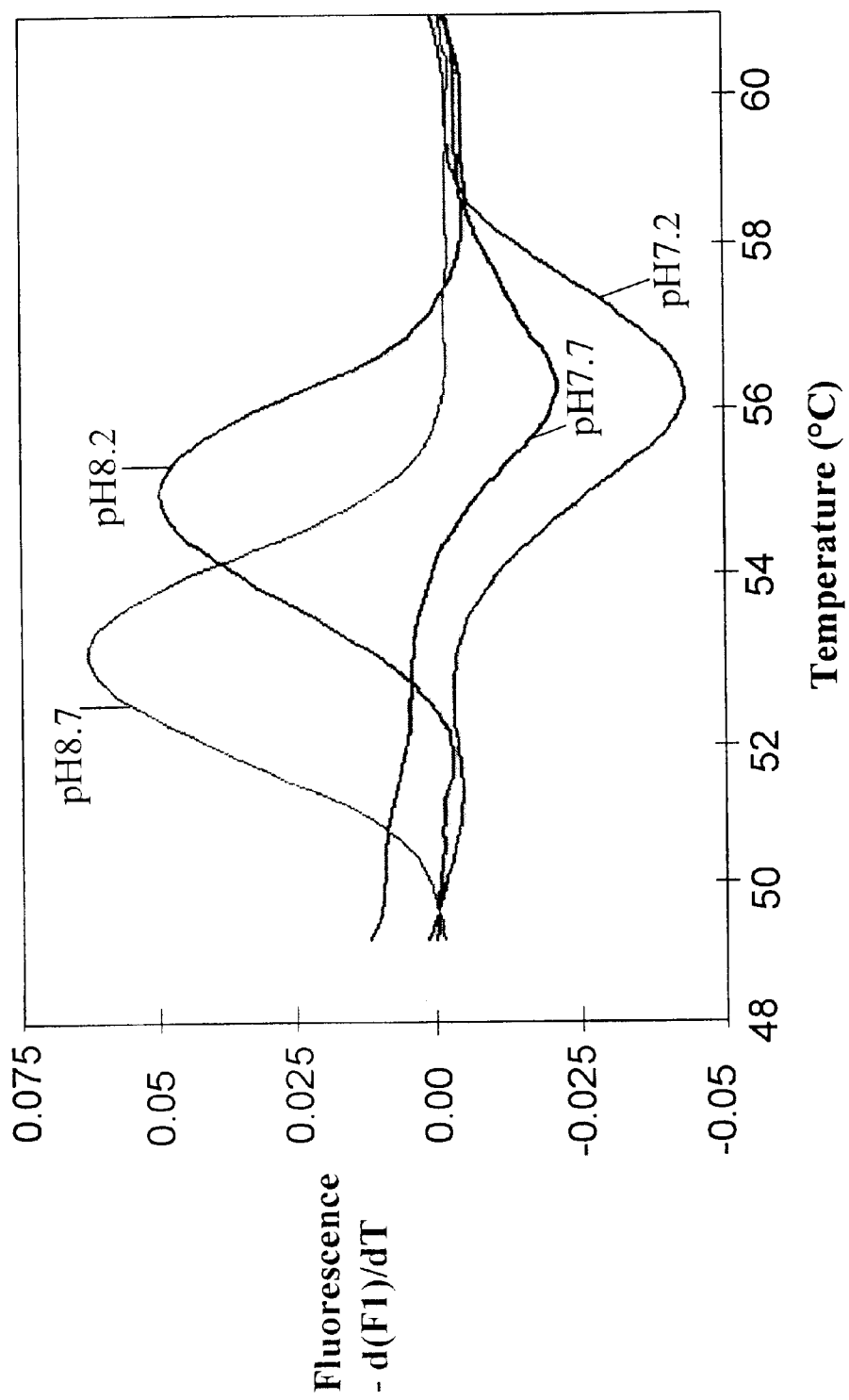

Melting curve analyses using Probe 1 and Target P (Table 3) were performed as in Example 4, except for varying the buffer pH and cation concentration. The effect of buffer pH was studied in a 100 mM KCL, 10 mM Tris solution titrated to the various pHs with HCl (FIG. 8a, closed diamonds). Comparison of relative signal strength is possible by comparison of peak area values of the melting curve data. The optimal pH is 7.4–8.0, with the best signal obtained at pH 7.6–7.8. The effect of buffer cation content was studied by adding various concentrations of KCl to a 10 mM Tris, pH 8.3 solution (FIG. 8b, closed circles). Signal was very low at KCl concentrations of 10 or 20 mM. Good signal was observed at 50–200 mM KCl, with the best result obtained at about 100 mM. Similar cation effects were obtained when the cation was provided as part of the buffer such as with, but not limited to, Tris+ and Tricine+. Good signal can be obtained using 100 mM Tris, pH 7.8, which is compatible with PCR.

EXAMPLE 14

Optimization of Dequenching Probes, and Interchangeability of Quenching and Dequenching by pH The probe and target of Set V (Table 4) were used to further study probe systems that dequench (increase signal) upon hybridization. Melting curve analysis was performed by heating the probe-target mixtures to 95° C. for 0 sec, cooling to 40° C. for 15 sec, followed by a ramp at 0.1° C./s to 94° C. with continuous monitoring.

Figure 9:
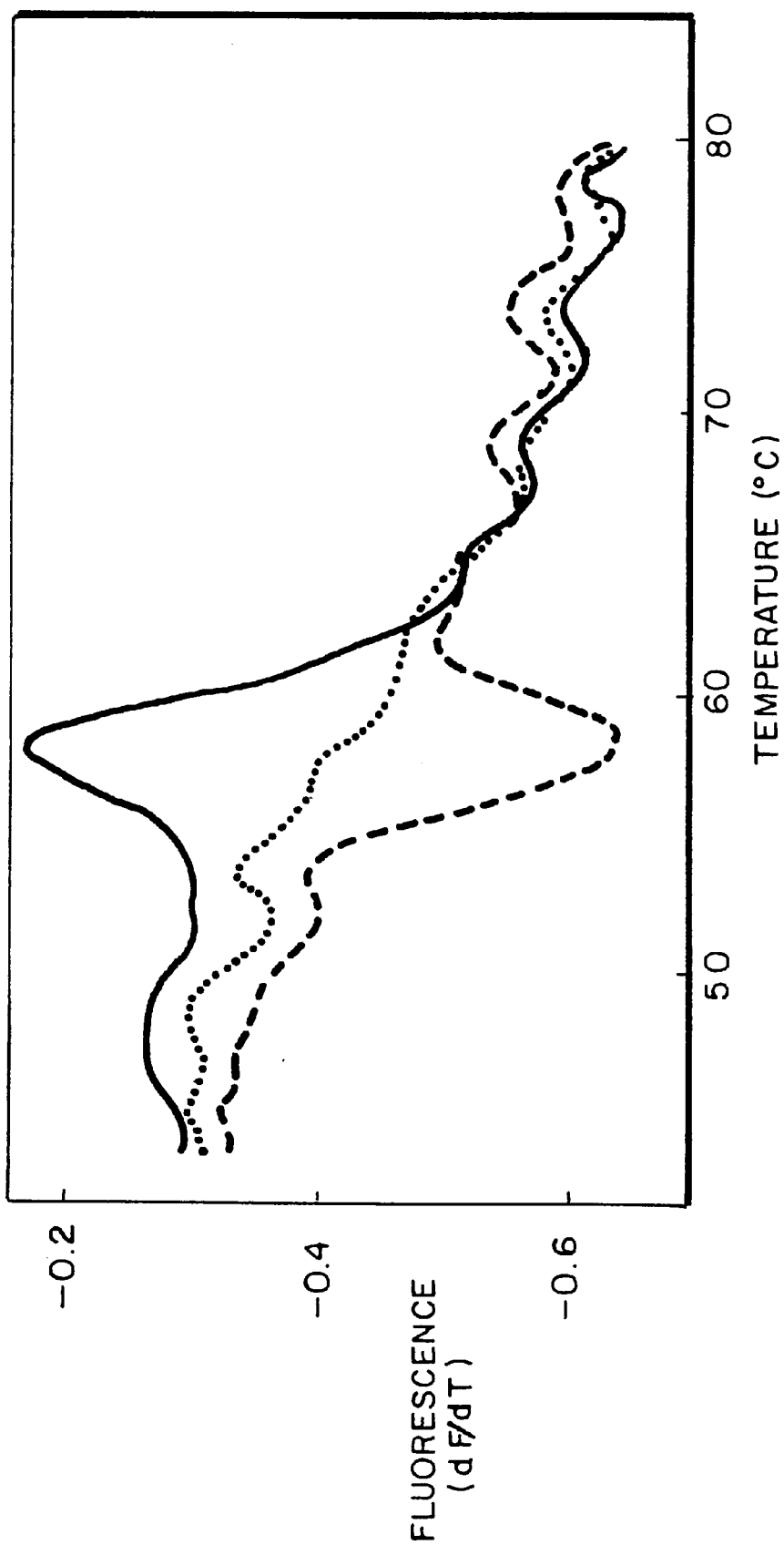
FIG. 9 is a plot of melting curve data for the dequenching probe, in which the level and direction of fluorescence change is affected by the pH of buffer. Curves for buffer pH 7.2, pH 7.7, pH 8.2, pH 8.8 are shown.

FIG. 9 demonstrates the influence of buffer pH on signal strength and the direction of signal change. In this figure, the buffer was 100 mM Tris with 500 µg/ml BSA. When the pH is more basic (alkali) than 8, the probe dequenches upon hybridization. However, when the pH is more acidic than 8, the probe quenches upon hybridization. In other words, quenching or dequenching is not entirely a property of the probe, or even of the probe/template combination, but also depends on the buffer conditions (cation concentration and pH). This is further exemplified in FIG. 8a (open diamond and open triangle symbols) in which pH ranges of 7.2–9.0 and 8.7–10.7 were studied by use of 10 mM Tris buffer, or 10 mM 2-amino-2-methyl-1-propanol buffer, respectively, in the presence of 160 mM KCL. Dequenching signal is obtained at pH 8.0–10.7, with best results obtained at or above pH 8.6. There was very little signal at a pH around 8.0, and slight quenching was observed at more acid pH. Buffers of 2-amino-2-methyl-1,3-propanediol can also be used to provide a basic buffer solution useful for this application.

FIG. 8b (open circles) shows the effect of cations on the dequenching signal. Signal is very low at 10–20 mM KCl, but strong at 50–320 mM KCL, with best results at 80–160 mM KCL. Similar cation effects were obtained with Li+, Na+, Cs+, tetramethylammonium+ions, or if the cation was provided as part of the buffer such as with, but not limited to, Tris+ and Tricine+. Good signal was also obtained using 200 mM Tris, pH 8.7–8.8 which is compatible with PCR and was utilized in Example 12. Compounds such as glycerol and tetrapentylammonium+ inhibited the dequenching signal.

Example 15

Dependence of Melting Peak Area on Probe Tm in Relation to the PCR Annealing Temperature Single-labeled probes with various Tms were used to study the relationship between probe Tm, PCR annealing temperature, and signal strength of fluorescence change upon probe-target melting. As in the previous examples, signal strength was assessed by relative peak area values obtained from melting curve data. The following six probes, labeled with a 5'-fluorescein and terminated with a 3' phosphate, were designed to be complementary to the region of the G845A polymorphism associated with hemochromatosis (Genbank Accession #Z92910):

| | |
|---|---|
| Probe-a (21 ntd) | As probe HCYP2 plus an additional 3' C residue |
| Probe-b (21 ntd) | As Probe-a, but 4 bases shifted toward the 3'-direction |
| Probe-c (17 ntd) | As Probe-a, but 4 bases truncated at the 3'-end |
| Probe-d (17 ntd) | As Probe-b, but 4 bases truncated at the 3'-end |
| Probe-e (13 ntd) | As Probe-c, but 4 bases truncated at the 3'-end |
| Probe-f (13 ntd) | As Probe-d, but 4 bases truncated at the 3'-end |

Figure 10:
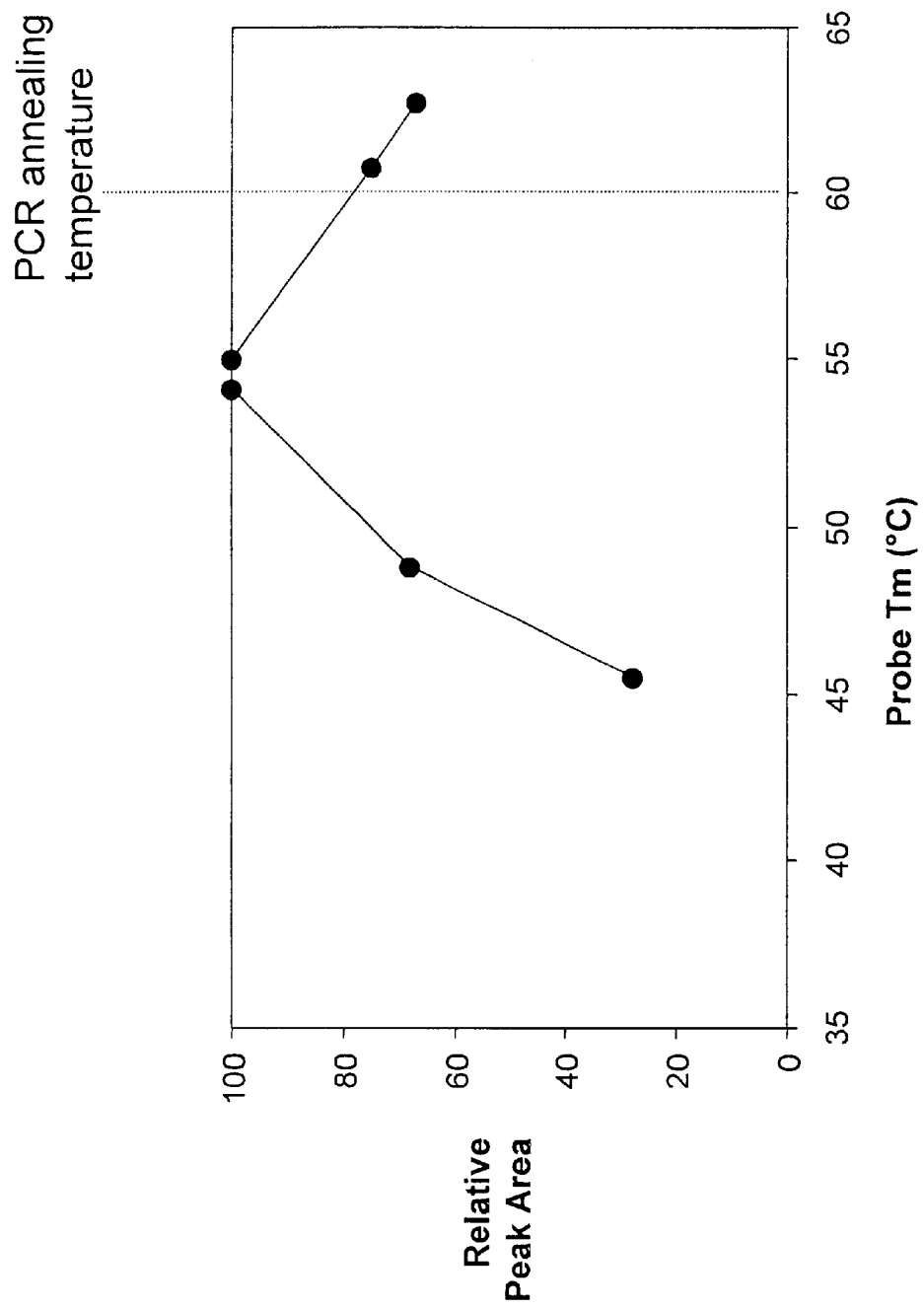
FIG. 10 is a plot of melting peak area vs probe Tm.

Asymmetric amplification was performed with 0.0625 µM of primer HCYR, and 0.5 µM of primer 5'GGCTGGATAACCTTGGCTGTA (SEQ ID NO:71) using the reaction mixture of Example 8 with TaqStart antibody (88 ng). Fifty PCR cycles of 94° C. for 0 sec, 60° C. for 10 sec and a 5° C./s ramp to 72° C. were performed, followed by final heating to 94° C., cooling to 35° C., holding for 10 sec, and continuous fluorescence acquisition at 0.1° C./s to 80° C. Peak areas for each derivative melting curve were determined and normalized by the peak areas obtained with the same probes against synthetic templates without PCR. The relative peak area values for probe-a and probe-e were determined by setting the peak area of probe-c to 100. The relative peak area values for probe-b and probe-f were determined by setting the peak area of probe-d to 100. Peak area values were plotted against Tm of the probes (FIG. 10). Maximum hybridization signal was observed when the probe Tm was about 5° C. below the PCR annealing temperature. In embodiments wherein it is not necessary to monitor fluorescence each cycle, the length of the probe should be adjusted so that the probe's Tm is lower than the PCR annealing temperature by 0–10° C., and most preferably lower by about 5° C. Primer Tms are often around the annealing temperature used in PCR, so the optimal probe Tm is also often about 5° C. less than primer Tms.

The decrease in signal strength seen with probes with Tms higher than the annealing temperature may be due to either probe hydrolysis during PCR, or to a decrease in PCR efficiency resulting from the probe blocking polymerase extension. The decrease in signal strength observed with probes with lower than optimal Tms may result from fewer available probe binding sites resulting from annealing of product strands during cooling, or due to secondary structure formation within a strand.

Although the invention has been described in detail with reference to preferred embodiments, variations and modifications exist within the scope and spirit of the invention as described and defined in the following claims.

What is claimed is:

1. A fluorescence-based probe system for analyzing a target nucleic acid consisting essentially of a single-labeled polynucleotide comprising a sequence generally complementary to a locus of the nucleic acid and a fluorescent label attached to a terminal nucleotide, wherein the terminal nucleotide is a base analog, whereby upon hybridization of the single-labeled polynucleotide to the locus of the nucleic acid the fluorescent label is positioned near a residue of the target nucleic acid with a resultant increase in fluorescent intensity of the fluorescent label.

2. The probe system of claim 1 wherein the base analog is selected from the group consisting of 5-nitroindole, 4-nitroindole, 6-nitroindole, 3-nitropyrrole, 5-iodo-cytidine, inosine, and nubluarine deoxynucleosides.

3. The probe system of claim 1 wherein the target nucleic acid has a C residue in a position complementary to the terminal nucleotide.

4. A probe for analyzing a target nucleic acid comprising a fluorescent detecting entity consisting essentially of a single-labeled oligonucleotide having a sequence generally complementary to a locus of the target nucleic acid and a fluorescent label linked to an internal residue of the oligonucleotide, the internal residue comprising a base analog, and wherein the sequence of the probe is selected so that upon hybridization of the probe to the locus of the target nucleic acid the magnitude of fluorescent emission from the fluorescent label is altered by hybridization of the probe to the target nucleic acid.

5. The probe of claim 4 wherein hybridization of the probe to the target nucleic acid places a G residue in positions +1, 0, or −1 relative to the position of the internal residue, and the fluorescent label is linked to the internal residue by a linker sufficiently flexible to allow quenching by the G residue.

6. A method for determining the presence of a target nucleic acid sequence in a biological sample comprising:
combining a single-labeled oligonucleotide probe with the sample, said probe having an oligonucleotide sequence generally complementary to a locus of the target nucleic acid sequence and a fluorescent label linked to a G residue of the oligonucleotide sequence, the fluorescent label exhibiting a hybridization-dependent fluorescent emission, wherein hybridization of the oligonucleotide probe to the target nucleic acid sequence alters interaction of the fluorescent label with the G residue, thereby increasing the fluorescent emission from the label,
illuminating the biological sample, and
monitoring the hybridization-dependent fluorescent emission.

7. The method of claim 6 wherein the G residue comprises a terminal residue of the oligonucleotide sequence.

8. The method of claim 7 wherein the locus of the target nucleic acid sequence has a C residue in the complementary location to the G residue.

9. The method of claim 8 wherein hybridization of the oligonucleotide sequence to the target nucleic acid creates an overhang adjacent to the C residue of the target nucleic acid.

10. The method of claim 9 wherein residues other than G are located at positions −1, +1, and +2.

11. The method of claim 7 wherein guanine residues are absent from positions −1 and +1 on the target nucleic acid sequence.

12. The method of claim 6 wherein the hybridization-dependent fluorescent emission is measured as a function of sample temperature.

13. The method of claim 6 wherein the probe and sample are combined in a solution having pH of >8.0.

14. The method of claim 13 wherein the solution has a Tris concentration of about 200 mM.

15. The method of claim 13 wherein the fluorescent label is selected from the group consisting of fluorescein, fluorescein derivatives, and fluorescein-cyanine conjugates, and the concentration of cations is about 50–200 mM.

16. The method of claim 13 wherein the solution further comprises a buffer selected from the group consisting of Tris+, Tricine+, 2-amino-2-methyl-1-propanol, and of 2-amino-2-methyl -1,3-propanediol.

17. The method of claim 6 wherein the hybridization-dependent fluorescent emission is monitored during asymmetric PCR.

18. The method of claim 17 wherein about 45 PCR cycles are performed, and a pair of PCR primers are provided in a 1:4 ratio.

19. The method of claim 17 wherein about 60 PCR cycles are performed, and a pair of PCR primers are provided in a 1:8 ratio.

20. A method of analyzing a sample comprising a target nucleic acid sequence, comprising the steps of
combining the sample and an oligonucleotide probe to create a target-probe mixture, wherein the probe includes a virtual nucleotide having a fluorescent label positioned so that the magnitude of fluorescent emission from the fluorescent label is altered by hybridization of the probe to the target nucleic acid sequence,
illuminating the mixture, and
monitoring the fluorescent emission from the fluorescent label.

21. The method of claim 20 further comprising the steps of:
combining the mixture with a pair of oligonucleotide primers, wherein the oligonucleotide primers are configured for amplifying a selected segment of the target nucleic acid sequence,
adding a polymerase, and
amplifying the selected segment of the target nucleic acid sequence.

22. The method of claim 21 wherein the pair of primers have an annealing temperature, and the probe has a Tm 0 to 10° C. below the annealing temperature.

23. The method of claim 21 wherein the fluorescent label is selected from the group consisting of fluorescein, fluorescein derivatives, and fluorescein-cyanine conjugates, the target nucleic acid sequence comprises a guanine residue in the complementary position to the virtual nucleotide, and the fluorescent emission is quenched upon hybridization of the oligonucleotide probe to the target nucleic acid sequence.

24. The method of claim 20 further comprising the step of amplifying a selected segment of the target nucleic acid sequence by a procedure selected from the group consisting of SDA, NASBA, CRCA, Q beta replicase mediated amplification, ICAN, and TMA.

25. The method of claim 20 wherein the fluorescent label is selected from the group consisting of fluorescein, fluorescein derivatives, cyanine derivatives, and fluorescein-cyanine conjugates, and hybridization of the probe to the target nucleic acid places the fluorescent label in a complementary position to a residue other than guanine and results in increased fluorescent emission.

26. The method of claim 25 wherein the residue other than guanine is adenine.

27. The method of claim 20 wherein the fluorescent emission is monitored as a function of temperature.

28. A method for determining the presence of a target nucleic acid sequence in a biological sample comprising:
combining the biological sample with a pair of primers configured for amplifying a selected segment of the target nucleic acid sequence and a fluorescent detecting entity consisting essentially of a single-labeled oligonucleotide probe,
wherein the single-labeled probe comprises an oligonucleotide having a sequence complementary to a locus of the selected segment of the target nucleic acid sequence, and having a fluorescent label exhibiting a sequence-specific hybridization-dependent emission attached thereto, wherein hybridization of the probe to the locus results in an increase in fluorescent emission of the fluorescent label,
adding a polymerase and amplifying the selected segment of the nucleic acid sequence through a plurality of amplification cycles,
illuminating the biological sample, and
monitoring the hybridization-dependent fluorescent emission.

29. The method of claim 28 further comprising the step of determining a maximum -df/dT as the probe dissociates from the target nucleic acid sequence.

30. The method of claim 28 wherein the fluorescent label is linked to a base of the oligonucleotide probe and the base is selected from the group consisting of, 4-nitroindole, 5-nitroindole, 6-nitroindole, and 3-nitropyrrole deoxynucleosides.

31. The method of claim 28 wherein the fluorescent label is linked to a base of the oligonucleotide probe and the base is selected from the group consisting of, inosine, 5-iodo-cytidine, and nubluarine deoxynucleosides, wherein a residue other than guanine is located on the target nucleic acid sequence at position +1 relative to the position of the label.

32. The method of claim 28 wherein the fluorescent label is attached to a guanine residue and the monitoring step includes monitoring the increased emission from the fluorescent label upon hybridization of the probe to the target nucleic acid.

33. The method of claim 28 wherein the fluorescent label is selected from the group consisting of cyanine dyes and LCRed 705.

34. The method of claim 28 wherein the fluorescent detecting entity is immobilized on a surface and the combining step includes placing the sample in contact with the surface.

35. The method of claim 28 further comprising providing a second fluorescent detecting entity consisting essentially of a second single-labeled oligonucleotide probe, wherein the second single-labeled oligonucleotide probe comprises a second oligonucleotide sequence generally complementary to a second selected segment of the target nucleic acid sequence and having a second fluorescent label linked to an end of the second oligonucleotide sequence, the second fluorescent label exhibiting a hybridization-dependent fluorescent emission at a wavelength different from the fluorescent emission of the first probe, wherein hybridization of the second oligonucleotide probe to the second selected segment results in altered fluorescent emission from the second label and the altered fluorescent signal is independent of fluorescent emission of the first fluorescent detecting entity, and monitoring the hybridization-dependent fluorescent emission of the second probe.

36. The method of claim 28 wherein the fluorescent label is attached to the 5' terminal nucleotide of the oligonucleotide, and further comprising the steps of combining the biological sample and the probe with a second oligonucleotide and a polymerase, and amplifying the target nucleic acid sequence, wherein the probe and the second oligonucleotide function as a pair of primers for amplification.

37. The method of claim 36 wherein the 5' terminal nucleotide is an A or T residue.

38. A kit for analyzing a biological sample comprising a nucleic acid sequence, comprising:

a. a fluorescent detecting entity consisting essentially of a single-labeled oligonucleotide probe having an oligonucleotide comprising a base analog, the base analog linked to a fluorescent label, wherein said probe is configured to hybridize to a single-stranded locus of the segment so that the magnitude of fluorescent emission from the fluorescent label is increased by hybridization of the probe to the locus; and b. components for amplification of the nucleic acid sequence.

39. The kit of claim 38 wherein the components include a pair of oligonucleotide primers configured for amplifying a segment of said nucleic acid sequence and a thermostable DNA polymerase.

40. The kit of claim 39 further comprising a second pair of primers configured for amplifying a second segment of said nucleic acid sequence comprising a second single-stranded locus; and a second fluorescent detecting entity consisting essentially of a second single-labeled oligonucleotide probe having a second oligonucleotide linked to a second fluorescent label, wherein said second probe is configured to hybridize to the second locus so that the magnitude of the fluorescent emission from the second fluorescent label is increased or decreased by hybridization of the second probe to the target nucleic acid sequence.

* * * * *